United States Patent [19]

Rogers

[11] Patent Number: 5,677,474
[45] Date of Patent: Oct. 14, 1997

[54] PRODUCING COMMERCIALLY VALUABLE POLYPEPTIDES WITH GENETICALLY TRANSFORMED ENDOSPERM TISSUE

[75] Inventor: John C. Rogers, Richmond Heights, Mo.

[73] Assignee: Washington University, St. Louis, Mo.

[21] Appl. No.: 478,360

[22] Filed: Jun. 7, 1995

Related U.S. Application Data

[63] Continuation of Ser. No. 385,866, Jul. 27, 1989, abandoned, which is a continuation-in-part of Ser. No. 225,800, Jul. 29, 1988, abandoned.

[51] Int. Cl.$^6$ .............................. A01H 1/06; C12N 15/05; C12N 15/09; C12N 15/29
[52] U.S. Cl. .................... 800/205; 800/205; 800/250; 800/DIG. 55; 800/DIG. 56; 800/DIG. 57; 536/24.1; 435/172.3
[58] Field of Search .................................. 800/205, 250, 800/DIG. 55, DIG. 56, DIG. 57; 536/24.1; 435/172.3, 69.1, 240.4, 69.7

[56] References Cited

U.S. PATENT DOCUMENTS 4,771,002  9/1988  Gelvin ..................................... 435/253

FOREIGN PATENT DOCUMENTS

| 0257472 | 2/1988 | European Pat. Off. |
| 0270356 | 6/1988 | European Pat. Off. |
| 0299552 | 1/1989 | European Pat. Off. |
| 0319353 | 6/1989 | European Pat. Off. |
| WO 83/01176 | 4/1983 | WIPO |
| WO 87/00865 | 2/1987 | WIPO |
| 89/03887 | 5/1989 | WIPO |

OTHER PUBLICATIONS

Huttly, et al.; A Wheat a–Amy2 Promoter is Regulated by Gibberellin In Transformed Oat Aleurone Protoplasts; EMBO Journal (1989); 8: 1907–1913.

Schell; Transgenic Plants as Tools to Study the Molecular Organization of Plant Genes; Science (1987); 237: 1176–1183.

Ellis, et al.; Maize Adh–1 Promoter Sequences Control Anaerobic Regulation; EMBO Journal (1987); 6: 11–16.

Czernilofsky, et al.: Fate of Selectable Marker DNA Integrated into the Genome of Nicotiana Tabacum; DNA (1986); 5: 101–113.

Rogers, et al.; Coordinate Increase in Major Transcripts from the High pI a–Amylase Multigene Family in Barley Aleurone Cells Stimulated with Gibberellic Acid; Journal of Biological Chemistry (1984); 259: 12234–12240.

Kursheed, et al.; Barley a–Amylase Genes; Journal of Biological Chemistry (1988); 263: 18953–18960.

Whittier, et al.; Nucleotide Sequence Analysis of Alpha–Amylase and Thiol Protease Genes that are Hormonally Regulated in Barley Aleurone Cells; Nucleic Acids Research (1987); 15: 2515–2535.

Rogers; Two Barley a–Amylase Gene Families Are Regulated Differently in Aleurone Cells; Journal of Biological Chemistry (1985); 6: 3731–3738.

YUMO, et al.: Hormonal Control of a Secretory Tissue; Current Topics in Developmental Biology, Chapter 4 (1971); 6:111–144.

King, et al.; Maize; Handbook of Plant Cell Culture (1984); 2: 69–91.

Devereux, et al.; A Comprehensive Set of Sequence Analysis Programs for the VAX; Nucleic Acids Research (1984); 12: 387–395.

Ausubel, et al. (eds. 1989); Current Protocols in Molecular Biology, Chapter 8.

Mundy, et al.; Selective Expressive of a Probable Amylase/Protease Inhibitor in Barley Aleurone Cells; Planta (1986); 169: 51–63.

Edens, et al.; Cloning of cDNA encoding the Sweet–Tasting Plant Protein Thaumatin and its Expression in *Excherichia Coli*; Gene (1982); 18: 1–12.

Bollum; Antibody to Terminal Deoxynucleotidyl Transferase; Proc. Natl. Acad. Sci. USA (1975); 72: 4119–4122.

Dellaporta, et al.; Molecular Biology of Plants; Cold Spring Harbor Laboratory; Cold Spring Harbor Laboratory Summer Course, Jun. 8–28, 1984.

Rogers, et al.; Isolation and Sequence Analysis of a Barley a–Amylase cDNA Clone; Journal of Biological Chemistry; (1983); 258: 8169–8174.

Jefferson, et al.; GUS Fusions; The EMBO Journal (1987); 6: 3901–3907.

Prioli, et al.; Plant Regeneration and Recovery of Fertile Plants from Protoplasts of Maize; Bio/Technology (1989); 7: 589–594.

Shillito, et al.; Regeneration of Fertile Plants from Protoplasts of Elite Inbred Maize; Bio/Technology (1989); 7: 581–587.

Rhodes, et al.; Genetically Transformed Maize Plants from Protoplasts; Science (1988); 240: 204–207.

Shimamoto, et al.; Fertile Transgenic Rice Plants Regenerated From Transformed Protoplasts; Nature (1989); 338: 274–276.

Ohta; High–Efficiency Genetic Transformation of Maize by a Mixture of Pollen and Exogenous DNA; Proc. Natl. Acad. Sci. USA (1986); 83: 715–719.

(List continued on next page.)

*Primary Examiner*—Douglas W. Robinson
*Assistant Examiner*—Thomas Haas
*Attorney, Agent, or Firm*—Foley & Lardner

[57] ABSTRACT

The synthetic capacities of endosperm tissue are harnessed, for the production of an exogenous polypeptide, via the transformation of a cereal or other monocotyledonous plant with a genetic construct comprised of a structural sequence encoding the polypeptide and, upstream therefrom with respect to the direction of transcription, a segment containing at least one regulatory element that effects or regulates expression of the structural sequence in endosperm tissue. Downstream of the structural sequence, the genetic construct also includes a segment that contains a terminal-processing signal for completion of the processing of nascent mRNA.

35 Claims, 23 Drawing Sheets

OTHER PUBLICATIONS

Colot, et al.; Localization of Sequences in Wheat Endosperm Protein Genes which Confer Tissue–Specific Expression in Tobacco; The EMBO Journal (1987); 6: 3559–3564.

Huttly, et al.; GA Regulated Expression From a Wheat a–Amylase Promoter in Oat Aleurone Protoplasts; Journal of Cellular Biochemistry (1988); Suppl 12C, UCLA Symposia on Molecular & Cellular Biology, 17th Annual Meetings; Feb. 28–Apr. 10, 1988; Abstract L600.

Goldsbrough et al.; "Expression of Maize Zein Genes In Transformed Sunflower Cells"; *Mol. Gen. Genet.*; 202:374–381 (1986).

Boston et al.; "Control of Maize Zein Gene Expression"; *Genetic Engineering*; vol. 9; pp. 61–74 (1988).

Schernthaner et al.; "Endosperm–specific Activity of a Zein Gene Promoter in Transgenic Tobacco Plants"; *The EMBO Journal*; vol. 7, No. 5 pp. 1249–1255 (1988).

Potrykus; "Gene Transfer to Cereals: an Assessment"; *Bio/Technology*; Jun. 1990.

Antonelli et al., *Theor Appl Genet* (1990) 80:395–401 "Genomic DNA can be Used With Cationic Methods . . . ".

Vandekerckhove, et al.; Enkephalins Produced in Transgenic Plants Using Modified 2S Seed Storage Proteins; Bio Technology (1989); pp. 929–932.

de la Pena, et al; 1987 (Jan.) Nature 325: 274–276.

Matzke et al 1984 EMBO J 3:1525–1531.

Colat et al 1987 EMBO J 6:3559–3564 (Dec.).

Maier et al 1987 EMBO J 6: 17–22 (Jan.).

Klein et al 1987 Nature 327: 70–73 (May).

Beck et al 1982 Gene 19:327–336.

Knox et al 1987 Pl Molec Biol 9: 3–17.

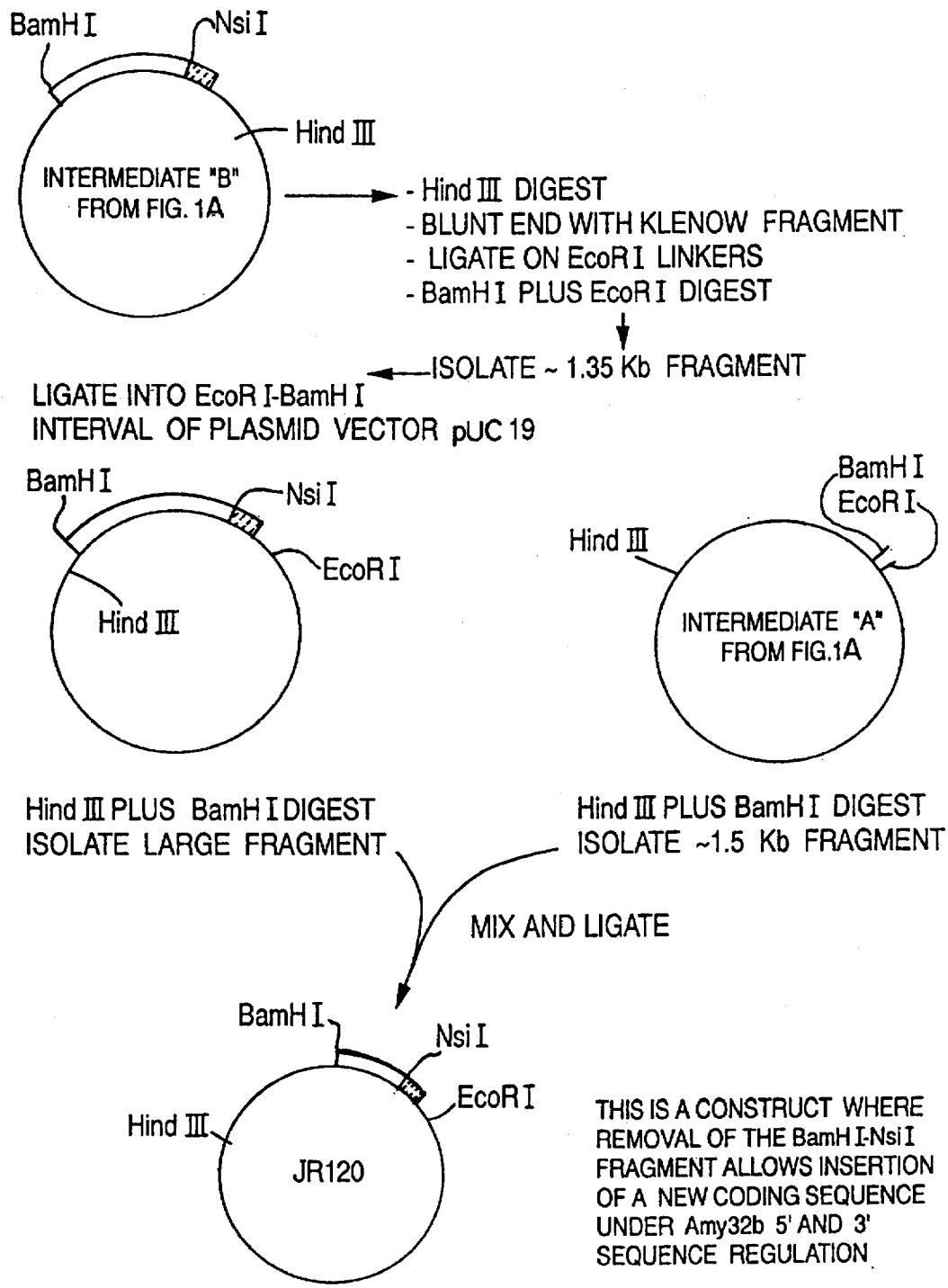

FIG. 5A(2)
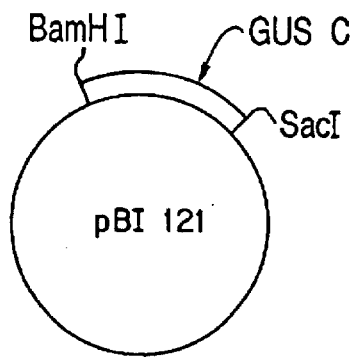
pBI121: FROM JEFFERSON,R.A., KAVANAGH,T.A., AND BEVAN,M.W. (1987) EMBO J. 13;3901-3907.
PLASMID PURCHASED FROM CLONTECH LABORATORIES, PALO ALTO, CA
- SacI DIGEST
- LIGATE ON PstI LINKER
- BamHI PLUS PstI DIGEST
- ISOLATE ~1.9 Kb FRAGMENT
→ MIX AND LIGATE
JR120
- BamHI PLUS NsiI DIGEST
- ISOLATE LARGE FRAGMENT
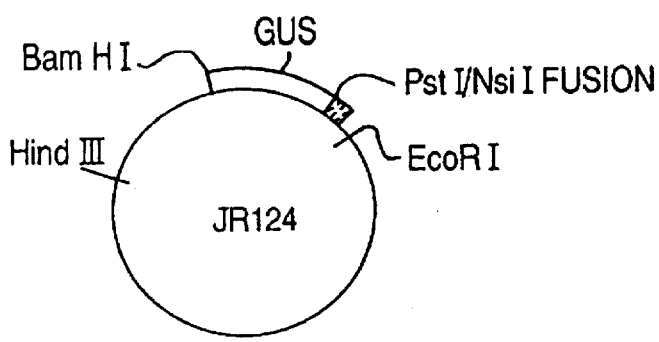

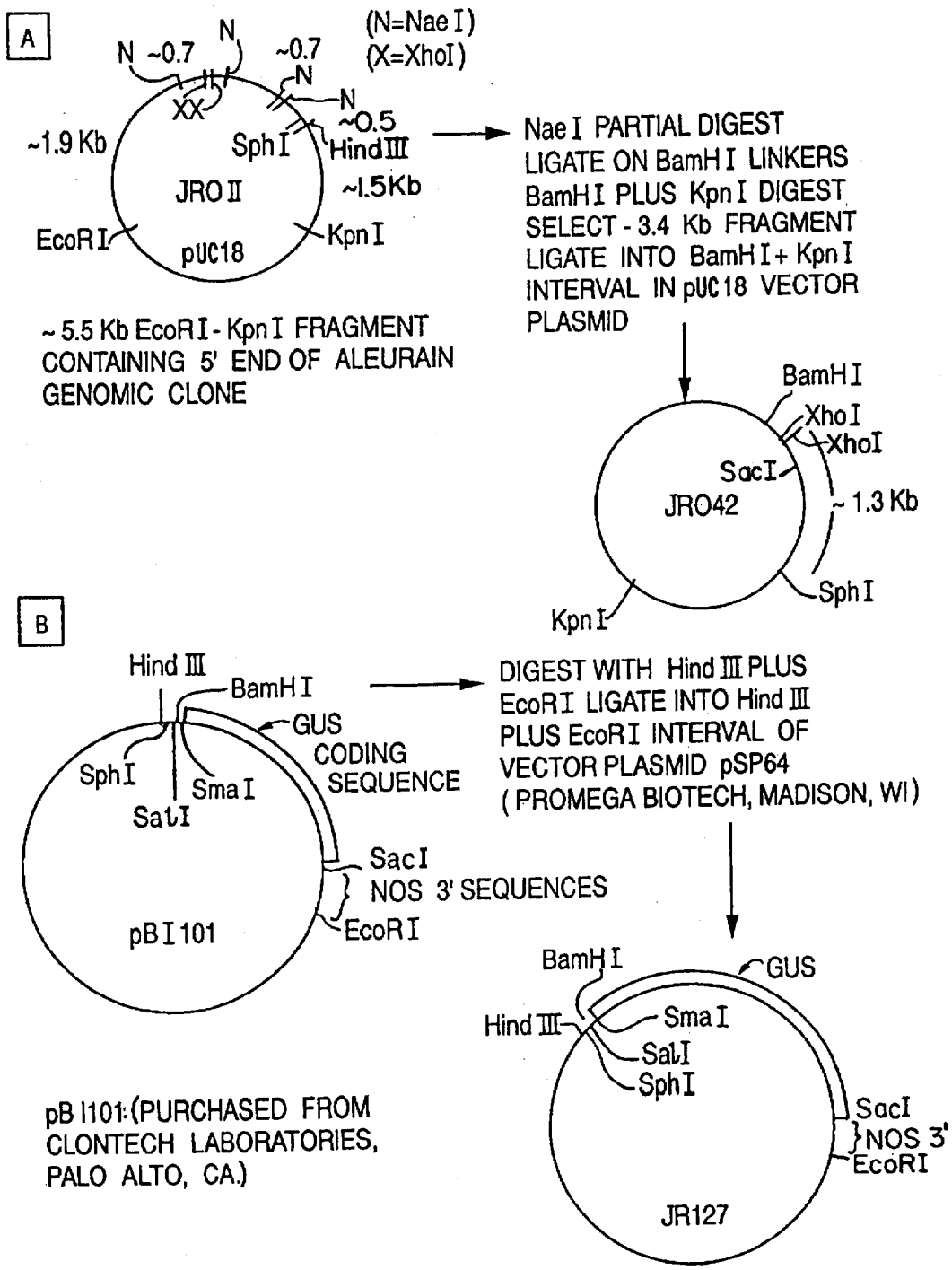
FIG. 5B(1)
CONSTRUCTION OF JR129, WHERE THE PROMOTER/UPSTREAM SEQUENCES AND PART OF THE CODING SEQUENCE FOR THE BARLEY GENE ALEURAIN (WHITTIER, R.F., DEAN, D. A., AND ROGERS, J. C. (1987) NUCLEIC ACIDS RES. 15, 2515 - 2535) ARE FUSED TO GUS:

FIG. 5B(2)
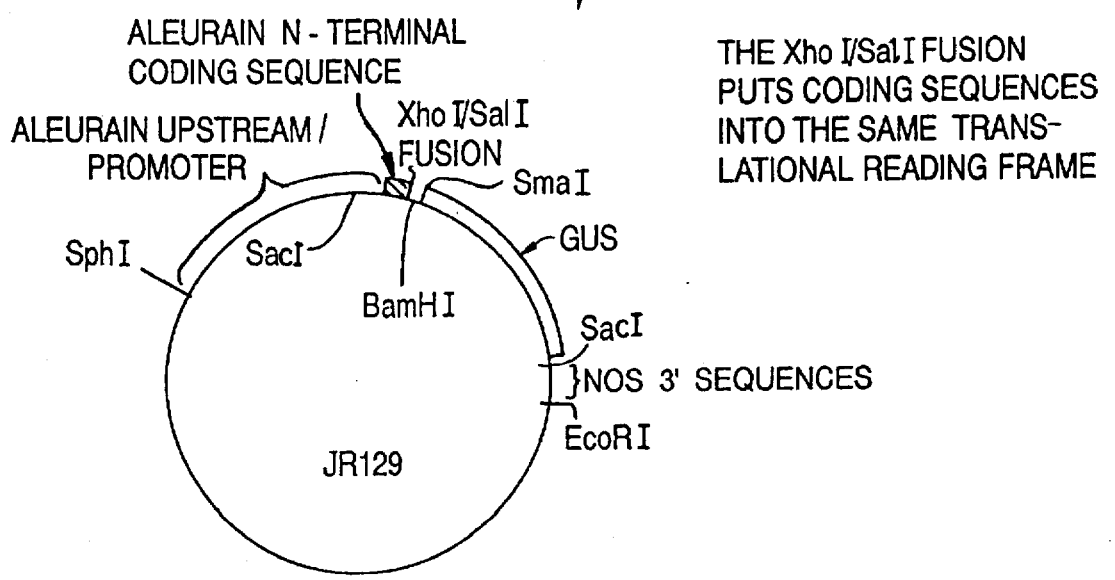

FIG. 5C(1)

CONSTRUCTION OF JR133, WHERE THE GUS CODING SEQUENCE IS FUSED TP THE N - TERMINAL CODING SEQUENCE OF THE BARLEY α- AMYLASE GENE, Amy6-4 (KLURSHEED, B., AND ROGERS, J. C. (1988) J. BIOL. CHEM. 263, 18953 - 18960). THE COMPLETED CONSTRUCT BRACKETS THE FUSED CODING SEQUENCE BETWEEN THE Amy6-4 UPSTREAM / PROMOTER REGION AND THE Amy6-4 3' SEQUENCES FOR RNA PROCESSING / POLY (A) ADDITION.

[A] FUSE GUS TO Amy6-4 3' SEQUENCES

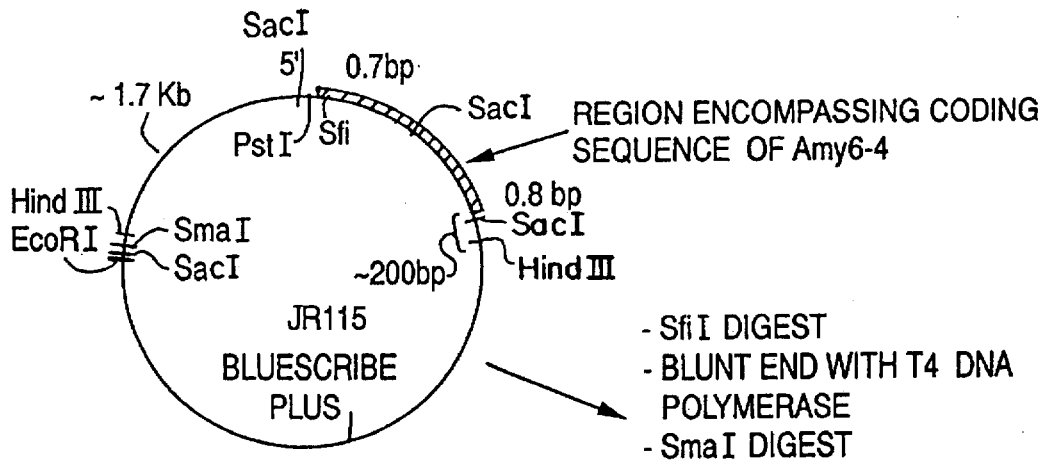

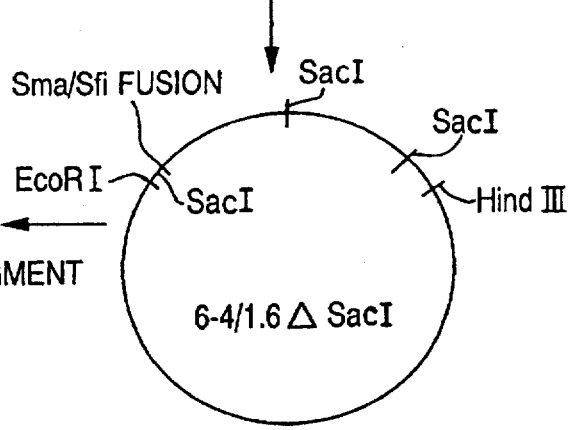

(SEE NEXT SHEET)

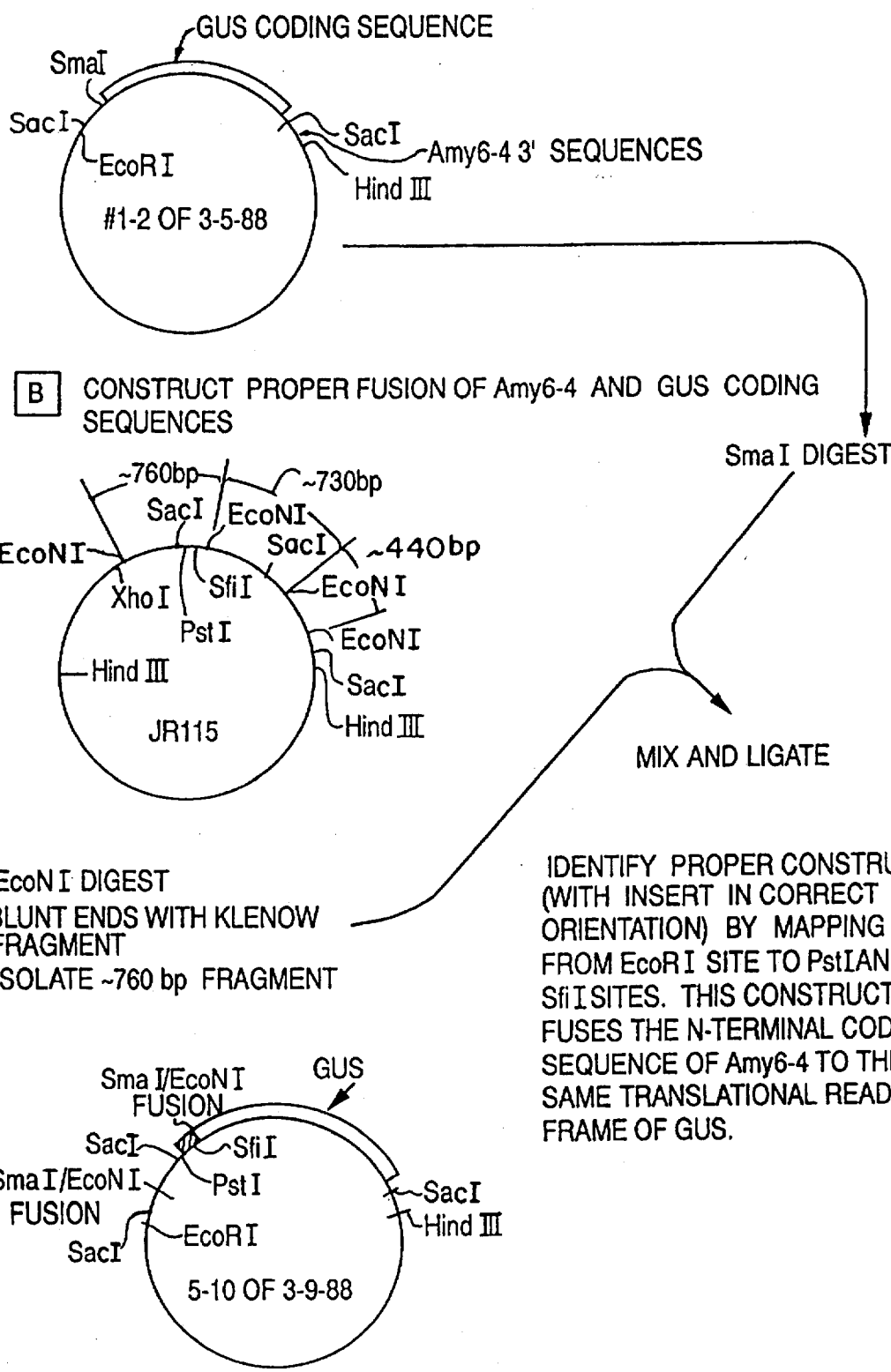
FIG. 5C(2)

FIG. 5C(3)

C  INSERT A LONGER PIECE OF Amy6-4 PROMOTER/UPSTREAM SEQUENCES

JR115:
- Sfi I DIGEST
- BLUNT END WITH T4 DNA POLYMERASE
- DIGEST WITH Hind III
- ISOLATE ~1.8 Kb FRAGMENT BLUESCRIBE PLUS:
- Hind III PLUS Sma I DIGEST
- ISOLATE LARGE FRAGMENT

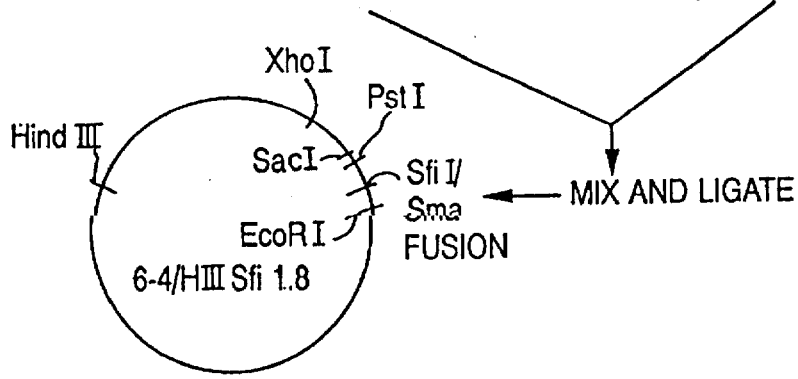

MIX AND LIGATE

- Pst I PLUS Hind III DIGEST
- ISOLATE SMALL FRAGMENT

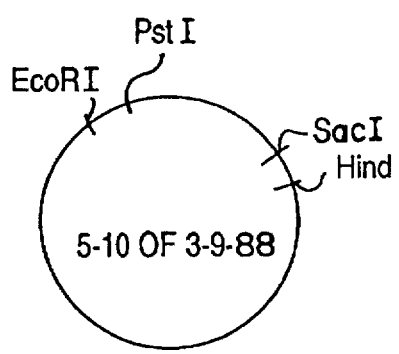

- Pst PLUS Hind III DIGEST
- ISOLATE SMALL FRAGMENT

BLUESCRIBE PLUS
- DIGEST WITH Hind III

- MIX 3 FRAGMENTS TOGETHER
- LIGATE
- IDENTIFY CORRECT CONSTRUCT BY MAPPING
  Hind III - Pst I,
  SacI
  Xho I - EcoRI:

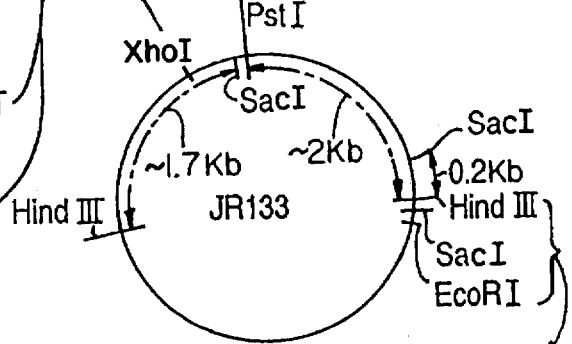

RESTRICTION SITES LOCATED IN PLASMID POLYLINKER

MEDIA

EXTRACTS 5,677,474

PRODUCING COMMERCIALLY VALUABLE POLYPEPTIDES WITH GENETICALLY TRANSFORMED ENDOSPERM TISSUE

This application is a continuation of Ser. No. 07/385,866, filed Jul. 27, 1989, now abandoned, which is a continuation-in-part of Ser. No. 07/225,800, filed Jul. 29, 1988, now abandoned.

BACKGROUND OF THE INVENTION

The present invention relates to obtaining genetically transformed monocotyledonous (monocot) plants that produce seeds comprised of endosperm tissue expressing exogenous, polypeptide-encoding DNA. The present invention also relates to the use of such endosperm tissue to produce exogenous proteins, including biologically active substances like insulin, tissue plasminogen factor, and human growth hormone.

The endosperm of a monocotyledonous plant is comprised of the aleurone layer and the starchy endosperm. These endosperm tissues develop from a single triploid cell, which is the product of the fusion of a sperm cell nucleus and two egg cell nuclei, an event that is separate from the fusion that gives rise to embryo tissues. Aleurone cells form a layer that surrounds the starchy endosperm of seeds produced by monocot plants, including the agriculturally important cereals. During germination, the plant embryo secretes gibberellic acid (GA), a hormone that causes the aleurone layer to synthesize and secrete large amounts of a limited number of hydrolytic enzymes. These enzymes degrade material, such as starch and protein, that is stored in the endosperm, resulting in the release of products used by the growing embryo.

For example, the aleurone layers from only ten half seeds of barley (cv. "Himalaya"), representing about a million aleurone cells, secrete more than 300 micrograms of the hydrolytic enzyme α-amylase in just 24 hours. Other cultivars used to produce malting for beer secrete three times this amount.

Despite this prodigious synthetic capacity, endosperm tissue has not been the object of extensive experimentation aimed at achieving expression of exogenous (foreign) DNA. Huttly and Baulcombe, *J. Cell. Chem.*, Suppl. 12C (1988), at page 207, report GA-regulated expression in oat aleurone protoplasts into which they introduced a genetic construct consisting of a wheat α-amylase promoter and a DNA sequence coding for the enzyme β-glucuronidase. The expression was transient only, and no suggestion was made as to how or even why aleurone-specific expression of exogenous DNA at a level above single protoplasts should be achieved.

SUMMARY OF THE INVENTION

It is therefore an object of the present invention to provide a method for producing valuable proteins by exploiting the synthetic capacity of aleurone tissue.

It is also an object of the present invention to provide a process for obtaining monocot seed containing a substance encoded by exogenous (foreign) DNA which is expressed by transformed endosperm.

It is yet another object of the present invention to provide a monocot plant that produces seeds comprised of endosperm tissue genetically transformed to express an exogenous DNA sequence coding for a polypeptide.

It is still another object of the present invention to provide a plant having a stably heritable phenotype that is characterized by the presence of aleurone tissue producing a foreign (exogenous) polypeptide.

In accomplishing these objects, there has been provided, in accordance with one aspect of the present invention, a method for obtaining seed comprised of genetically transformed endosperm tissue, comprising the steps of (A) providing a genetic construct comprised of (i) a regulatory element which is expressed at high levels in an endosperm cell; (ii) at least one DNA sequence that encodes a polypeptide, which DNA sequence is under the transcriptional control of the regulatory element; and (iii) a terminal-processing signal positioned downstream of the DNA sequence with regard to direction of transcription, (B) injecting the genetic construct into a floral tiller of a cereal plant prior to anthesis in the plant; and thereafter (C) assaying seeds from the injected plant for the presence of an expression product of the DNA sequence in the endosperm of any of the seeds, thereby to identify a seed comprised of genetically transformed endosperm tissue. In a preferred embodiment, step (C) of the process comprises assaying for the expression product by using an antibody that recognizes the product. In another preferred embodiment, the DNA sequence of the genetic construct has a guanine and cytosine (G+C) content that is greater than 50%.

In accordance with another aspect of the present invention, a process has been provided for producing a polypeptide, comprising the steps of (A) producing genetically transformed endosperm tissue that expresses a genetic construct as described above and (B) isolating a polypeptide that is the product of such endosperm-based expression. In one preferred embodiment, the aforesaid process comprises isolating exogenous protein from the endosperm of seeds obtained from a substantially uniform population of cereal plants. In another preferred embodiment, the process comprises isolating a polypeptide expression product of genetically transformed endosperm tissue from medium in which the tissue is cultured.

In accordance with yet another object of the present invention, there has been provided a differentiated monocotyledonous plant that produces seeds comprised of endosperm tissue, such as aleurone tissue, genetically transformed to express an exogenous DNA sequence which encodes a polypeptide. In a preferred embodiment, the plant is one of a substantially uniform population of monocotyledonous plants that produce seed comprised, respectively, of endosperm containing an exogenous protein. In another preferred embodiment, the exogenous DNA sequence codes for a polypeptide also encoded by a naturally-occurring gene but that has a guanine and cytosine (G+C) content that is higher than that of the naturally-occurring gene.

There has also been provided, in accordance with still another object of the present invention, seed of a monocotyledonous plant, e.g., wheat, barley, oats, sorghum, rye, millet, rice, maize, sugar cane and coconut palm, which seed contains endosperm comprised of an exogenous polypeptide.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 5A–5C is a schematic diagram illustrating the manufacture of genetic constructs suitable for use with the GUS probe in the present invention. FIG. 5A illustrates the construction of plasmid JR124; FIG. 5B illustrates the construction of plasmid JR129; and FIG. 5C illustrates the construction of plasmid JR133.

FIG. 8B shows the results from different digests of DNA from plants transformed with the JR133 construct hybridized with the GUS coding sequence probe. FIG. 8C presents the results of similar analyses utilizing different restriction enzymes for DNA from two of the plants (2G7 and 2G10).

FIG. 12A provides the methylation pattern of the 133-series GUS-positive parent DNA fragments in 2G6 compared with control DNA, as assessed by digestion with different enzymes. FIG. 12B provides the results of a similar digestion of GUS-hybridizing DNA in 2G8, 4F1, and 4G1.

FIG. 13B provides the electrophoretic results of the undigested GUS-hybridizing fragments in progeny 2G7#3 and 5A7#8 compared with those fragments resulting from digestion with BamHI or EcoRI.

DETAILED DESCRIPTION OF PREFERRED EMBODIMENTS

Figure 1A:
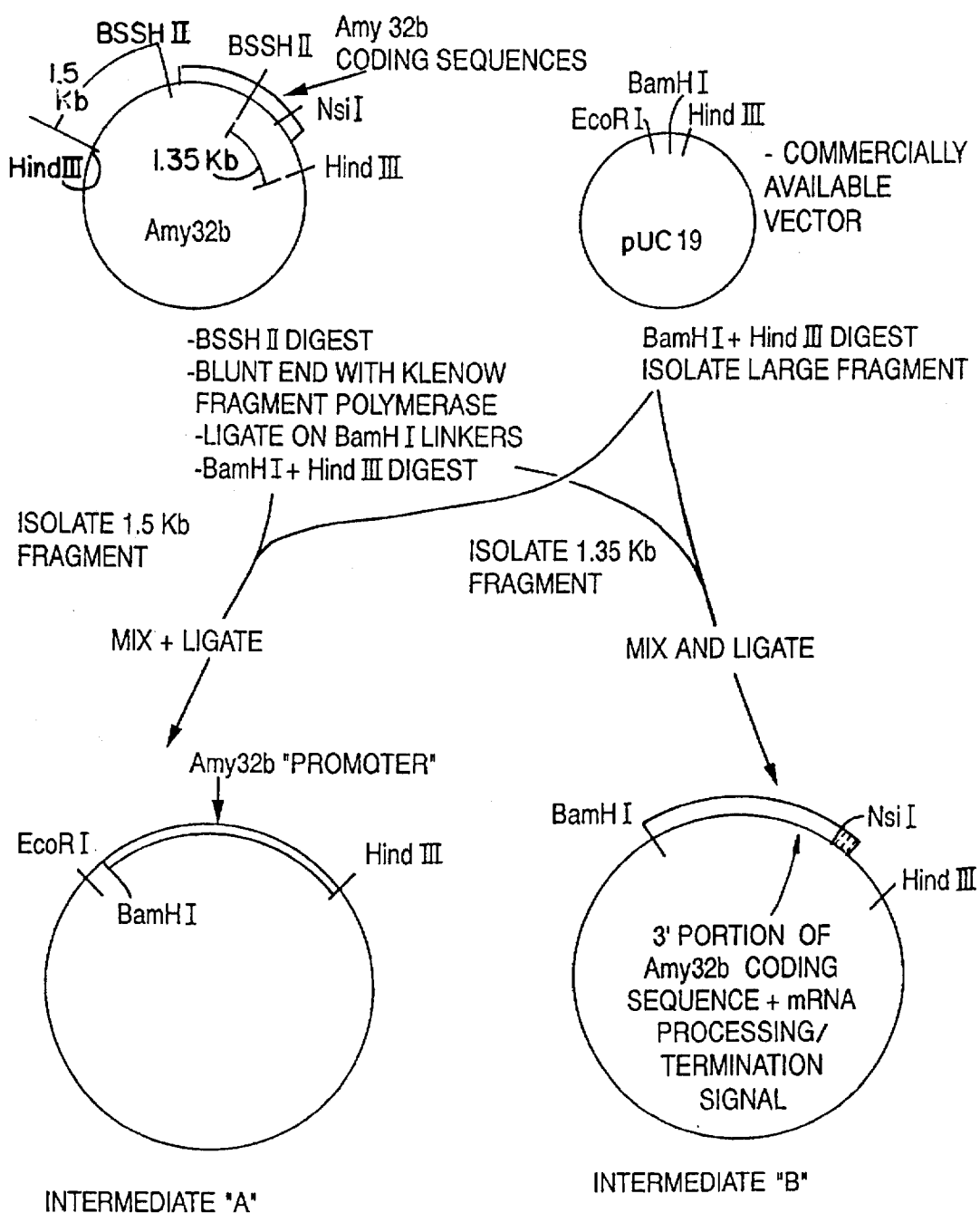
FIG. 1 is a schematic diagram illustrating the manufacture of a genetic construct suitable for use in accordance with the present invention.

Pursuant to the present invention, the synthetic capacities of endosperm tissue are harnessed, for production of an exogenous polypeptide, via the transformation of a cereal or other monocot plant with a genetic construct comprised of a DNA sequence (a "structural sequence") encoding the polypeptide and, upstream therefrom with respect to the direction of transcription, a DNA segment containing at least one regulatory element that effects or regulates expression of the structural sequence in endosperm tissue. Downstream of the structural sequence, the genetic construct also includes a DNA segment that contains a terminal-processing signal for completion of the processing of nascent mRNA.

More specifically, the phrase "terminal-processing signal" denotes a nucleotide sequence that is recognized, during post-transcription processing of mRNA in vivo, as indicating where a precursor mRNA molecule should be cleaved to yield a mature mRNA species which will be translated. A segment containing a terminal-processing signal can be obtained by comparing cDNA encoding an endosperm-expressed product, such as that for α-amylase, protease, protease inhibitor, or α-glucanase, with the genomic DNA coding for the same product, thereby to identify the 3' terminus of the cDNA. By isolating a genomic DNA segment comprising 50 to 100 base-pairs on either side of the aforementioned 3' terminus, one is assured of obtaining a segment with the terminal-processing signal.

Conventional techniques are available for making a <regulatory element/structural sequence/terminal-processing signal> fusion product, as described, e.g., by Schell, *Science* 237: 1176–83 (1987); Ellis et al., *EMBO J.* 6: 11–16 (1987) and Czernilofsky et al., *DNA* 5: 101–13 (1986). In this context, the phrase "regulatory element" denotes a nucleotide sequence that influences transcription of a structural sequence by influencing the movement of an RNA polymerase enzyme along the DNA template undergoing transcription. A preferred regulatory element, referred to here as a "promoter," includes (i) a site of initial recognition, prior to binding, between an RNA polymerase molecule and the DNA chain, (ii) a site for RNA polymerase binding and (iii) a site for initiation of transcription.

As indicated above, expression of a regulatory element suitable for the present invention should be especially strong in, or specific to, endosperm cells. Such a regulatory element can be obtained using cDNA produced from messenger RNA molecules (mRNAs) that are found exclusively in aleurone tissue, or at least are present at some stage of development or activation stage in endosperm tissue in amounts some 50-times or greater than corresponding amounts in either leaf and root tissues. Illustrative suitable promoters of this sort are the promoters for the low-pI α-amylase gene (Amy32b) as described by Rogers and Milliman, *J. Biol. Chem.* 259: 12234–12240 (1984), the high-pI α-amylase gene (Amy6-4) characterized by Khursheed and Rogers, *J. Biol. Chem.* 263: 18953–18960 (1988), and the promoter for a barley thiol protease gene ("Aleurain") as described by Whittier et al., *Nucleic Acids Res.* 15:2515–2535 (1987).

More particularly, total mRNA can be isolated from endosperm cells, and poly(A) RNA selected and used to produce cDNA by reverse transcription, via known methodology described, for example, by Rogers, *J. Biol. Chem.* 260:3731–38 (1985) (hereafter "Rogers (1985)"), the contents of which are hereby incorporated by reference. If the endosperm tissue is from the aleurone layer, the step of isolating total mRNA can optionally be preceded by a prolonged stimulation of the aleurone cells with GA, thereby to enhance the content of mRNA species transcribed under the control of a regulatory element that is GA-sensitive and, hence, presumably expressed in aleurone cells.

The cDNA thus produced is used to probe genomic DNA from a target monocot, such as a cereal crop (wheat, barley, oat, sorghum, rye, millet and rice), maize, sugar cane or coconut palm, in order to identify a structural sequence responsible for an abundant endosperm mRNA species represented in the cDNA. A segment of genomic DNA bordering the 5'-end of the structural sequence can then be isolated and incorporated into a genetic construct wherein the segment is fused to a structural sequence encoding a "marker" polypeptide which can be readily detected, e.g., using an antibody which recognizes an epitope presented by the polypeptide. A genomic-DNA segment of this sort that is on the order of 1.5 kilobases (kb) in length can be expected to include at least a promoter which can be employed as the regulatory element in the present invention.

The construct thus produced is used to transform a monocot plant so that detection of the marker can serve as an assay for the presence of a suitable regulatory element in a segment isolated, as described above, from genomic DNA. The same basic approach can also be used to introduce marker-encoding sequences into plants for varietal identification purposes, e.g., in the context of distinguishing malting barleys which have heretofore been differentiated only with difficulty.

More generally, the use of a non-antibiotic marker, as described herein, to screen plant transformants represents a departure from conventional practice, whereby transformants are screened on the basis of resistance to kanamycin or some other antibiotic. The latter approach requires expensive and complex facilities for the growth of large numbers of seedlings on precisely defined media into which the antibiotic is introduced. The high intrinsic resistance of cereals to antibiotics like kanamycin also means that the sensitivity of selection of transformants will be low, and that the false-positive rate will be high.

In conjunction with screening of transformants as described above, it is preferred that the transformants also be screened for the presence of methylation at adenine and cytosine bases. Transformants characterized by relatively extensive adenine methylation in the sequence GATC are less likely to maintain transforming DNA that is stably heritable. Accordingly, transformants are preferred in which the inserted DNA has undergone comparatively little methylation of adenines, but show some methylation of cytosine residues. These criteria of methylation pattern are readily assessed by using restriction enzymes with different sensitivities to methylation, such as MboI and Sau3AI, or MspI and HpaII.

A preferred means of transforming a monocot plant, pursuant to the present invention, entails injecting the construct into floral tillers of the target plant and then screening for transformed seeds produced by the injected tillers. In accordance with this approach, aliquots of an aqueous solution that contains the genetic construct are injected, prior to anthesis but after meiosis, into the hollow space above each developing inflorescence; total injected volume is typically around 300 µl. After injection in this manner, a floral tiller is allowed to grow to maturity and to produce seeds by self-fertilization or, in the event of self-incompatibility, by cross-pollination with other injected tillers. By this approach, transformation frequencies can be achieved that are sufficient to permit the development, via the selection method described herein, of genetically-modified plants which express exogenous DNA in endosperm tissue.

Whatever transformation technique is employed, seed from a putative transformant can be tested for the expression of foreign DNA by first separating the seed into an embryo-containing portion and a tip portion representing about 20% of the seed distal to the embryo. The latter portion is incubated in a suitable medium, which is thereafter tested, e.g., via an ELISA-type assay, to detect the presence of the polypeptide coded for by an exogenous structural sequence.

When the desired expression product is detected, the embryo-containing portion of the seed can be planted to obtain a differentiated monocot plant which can ultimately produce seeds comprised of endosperm tissue expressing the exogenous structural sequence. By conventional plant breeding techniques, the desired exogenous DNA sequence can be manifested in a homozygous condition and be capable of being passed on to subsequent generations. In a preferred embodiment of the present invention, a plurality of such transformed seeds are planted to obtain a stand or population of plants, preferably cereal plants, that is substantially uniform to the extent that most or all of the plants in the stand produce seed containing the desired exogenous protein. The plants can be harvested, and the desired protein extracted from the seed, in the course of an otherwise ordinary agricultural operation.

Alternatively, transformed seed of the present invention can be used as the source of endosperm cells for culturing in a suitable medium, whence a desired polypeptide synthesized and excreted by the cultured cells can be extracted. For example, the technology for isolating and culturing endosperm tissue has long been available, as evidenced by Yomo and Varner, CURRENT TOPICS IN DEVELOPMENTAL BIOLOGY 111–44 (Academic Press 1971) (aleurone tissue) and 2 HANDBOOK OF PLANT CELL CULTURE Ch. 3 (Macmillan 1984) (starchy endosperm tissue).

The range of structural sequences that can be employed in the present invention encompasses, in addition to synthetic sequences, genes or portions of genes that encode products ordinarily made by plants. Typical of such products is the protein thaumatin, found in arils of the fruit of West African plant *Thaumatococcus daniellii*, which is the sweetest known substance and, hence, a commercially valuable food additive. By the same token, structural sequences that code for various bacterial and fungal proteases, themselves useful detergent components, are suitable for use according to the present invention.

More generally, structural sequences cloned from a variety of prokaryotic and eukaryotic sources are also suitable in this context. Exemplary of such cloned sequences are those coding for hormones like insulin, bovine and human growth hormone, erythropoietin, atrial natriuretic factor, and the various colony stimulating factors (M-CSF, G-CSF, GM-CSF, interleukin-3, etc.); other growth and regulatory factors such as epidermal growth factor, insulin-like growth factor-1 and -2, nerve growth factor, transforming growth factor-α and -β and platelet-derived growth factor; the interferon proteins IFN-α and IFN-β; and proteins that are classified as monokines, such as interleukin-1α, interleukin-1β and tissue necrosis factor, or lymphokines, like interleukin-2 and IFN-γ.

It is preferred that the exogenous, polypeptide-encoding DNA used, according to the present invention, to produce transformed aleurone tissue should be rich in the bases guanine (G) and cytosine (C), in the sense that the (G+C) content of the DNA is higher than 50%, and preferably in the range of 60% to 65%, as determined from the DNA sequence. The class of structural DNAs satisfying this requirement includes virtually all studied cDNAs and genomic clones representing naturally-occurring genes expressed in aleurone tissue. See Khursheed and Rogers, *J. Biol. Chem.* 263: 18953–18960 (1988); Whittier et al., *Nucleic Acids Res.* 15: 2515–2535 (1987). For other eukaryotic and prokaryotic DNAs that are not (G+C)-rich in native form, synthetic or mutant DNA segments can be obtained that code for the polypeptide of a naturally-occurring gene but that are modified in such a manner that the (G+C) content is increased above 50%, and more preferably to 60%–65%.

The polypeptide-encoding DNA segment sequence can be modified, for example, using a computer program like "Codon Preference," available from the University of Wisconsin Genetics Computer Group [see Devereaux et al., *Nucleic Acids Res.* 12: 387–395 (1984)], to have increased (G+C) content while still encoding the same polypeptide. Once a desired polypeptide-encoding DNA sequence is determined, the encoding sequence can be synthesized by mutation of the cloned cDNA or genomic DNA [see, e.g., *CURRENT PROTOCOLS IN MOLECULAR BIOLOGY*, Chapter 8 (Ausabel, et al., eds. 1989)] or by synthesis via ligation of long (>100 base pairs) synthetic oligonucleotides. See Ausabel et al., supra, at pages 8.2.8 to 8.2.13.

It is also preferred that the exogenous DNA employed in transforming aleurone tissue pursuant to the present invention should not be methylated at adenosine bases. For purposes of producing usable amounts of exogenous DNA, therefore, a cloning system that does not methylate adenine is preferably employed. For example, all enteric bacteria possess the so-called dam restriction/methylation enzyme that methylates adenine at all GATC sites; it is for this reason that all plasmids grown in wild-type *E. coli* strains have every GATC site methylated. Dam⁻ *E. coli* strains are readily available commercially, for example, from Stratagene, La Jolla, Calif. (strain GM48), to use in cloning exogenous DNA for the present invention.

The present invention is further described below with regard to the following illustrative examples.

EXAMPLE 1

Production of Genetic Constructs

To form DNA coding for a marker polypeptide, the nucleotide sequence encoding prothaumatin protein, minus the signal peptide (i.e., the portion involved in the transport of the protein into the rough endoplasmic reticulum) and first seven amino acids of the mature protein, was fused in frame at the codon for the eighth thaumatin amino acid to a sequence coding for the signal peptide portion and first seven amino acids of the so-called "probable amylase/protease inhibitor" (PAPI) barley protein described by Mundy and Rogers, *Planta* 169: 51–63 (1986) (hereafter "Mundy & Rogers (1986)").

Prothaumatin cDNA was obtained for this purpose from a plasmid, pUR528, produced by Edens et al., *Gene* 18:1–12 (1982) (hereafter "Edens (1982)"), the contents of which are hereby incorporated by reference. Prothaumatin-encoding DNA can be synthesized, using conventional methodology, from the nucleotide sequence disclosed by Edens (1982). Alternatively, pUR528 can be obtained for research purposes from Unilever Research Laboratories (Vlaardingen, the Netherlands).

Figure 1B:
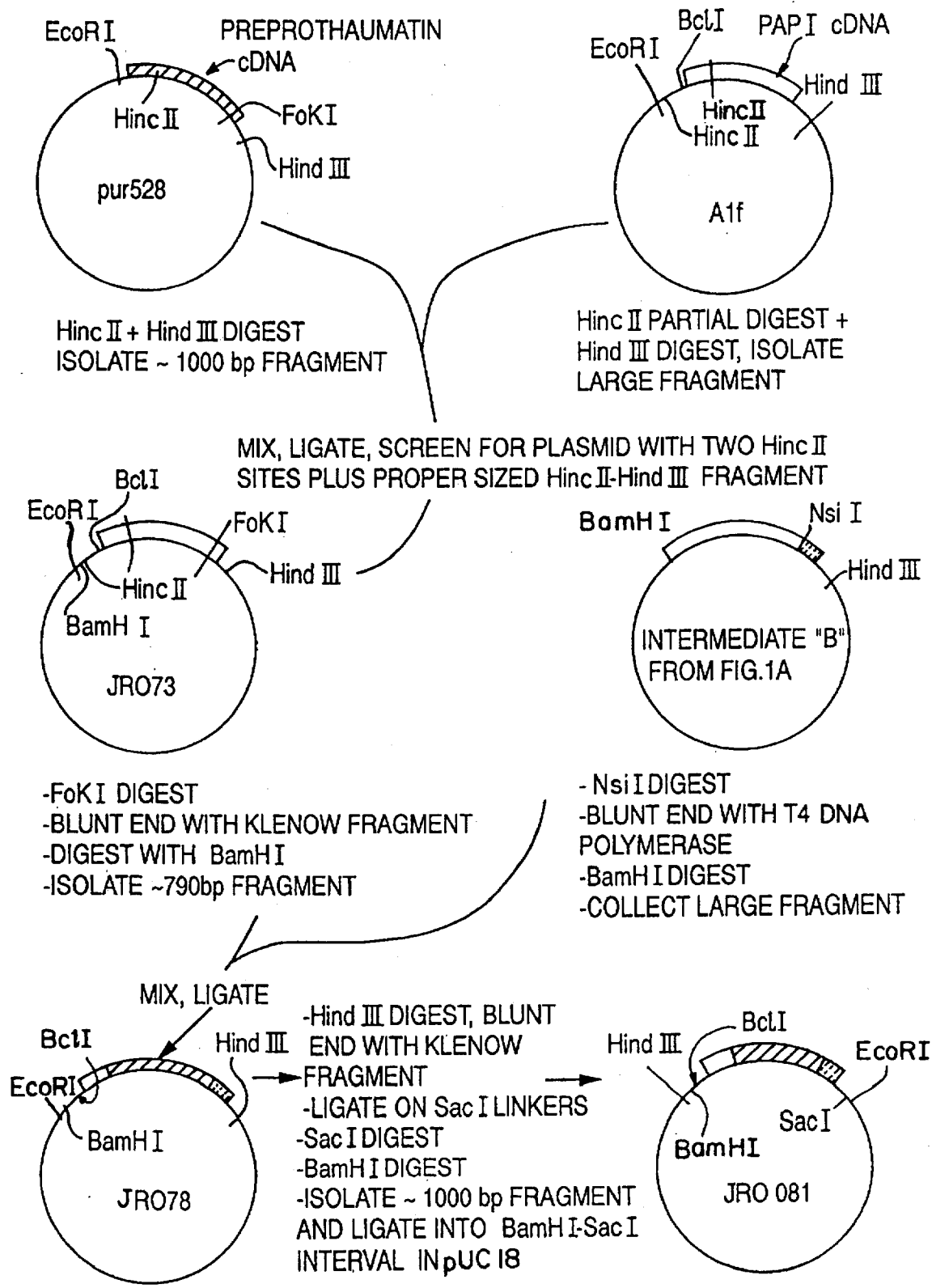
Figure 1C:
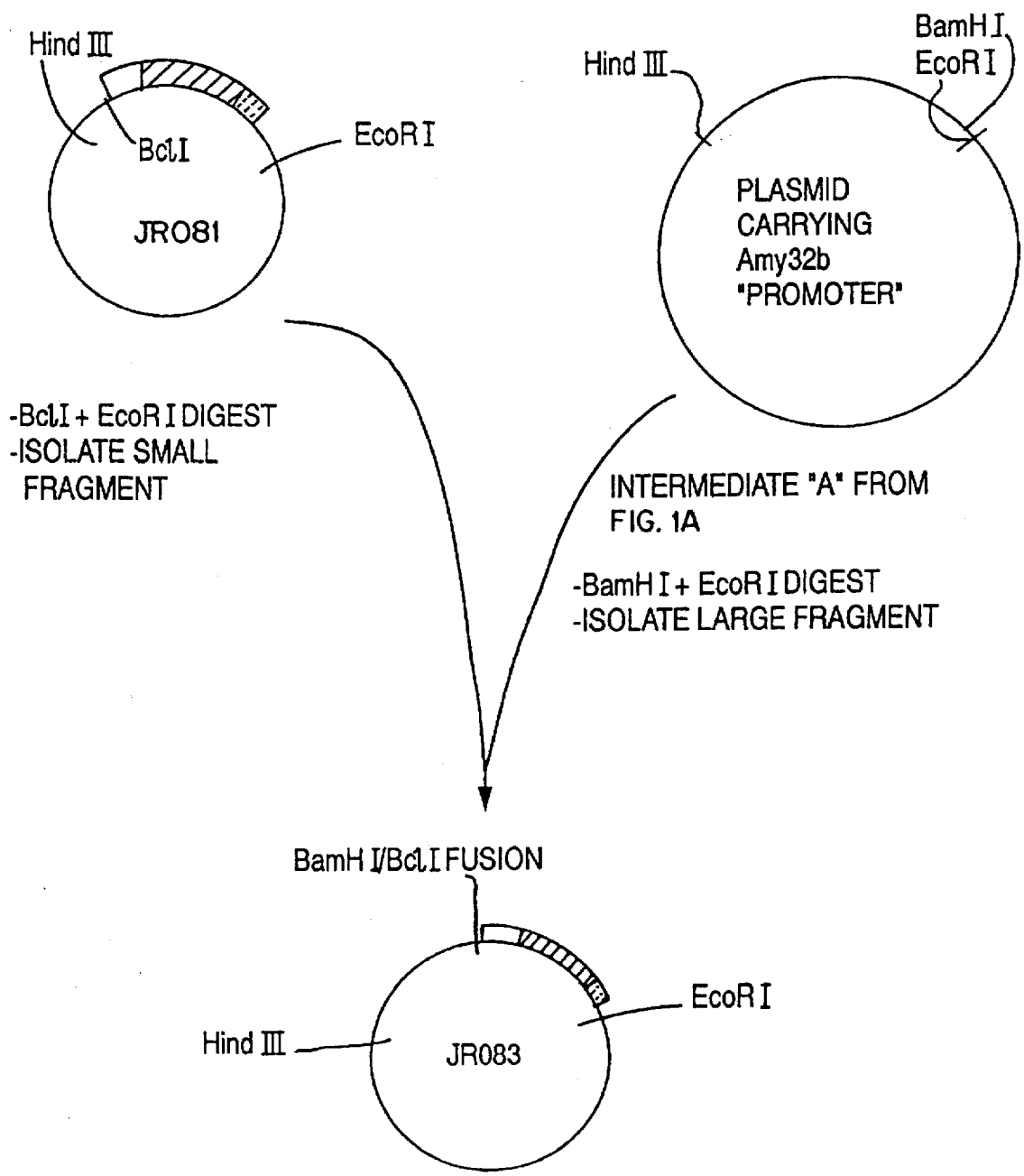

FIG. 1 depicts the approach used in producing genetic constructs that incorporate the above-mentioned marker sequence (designated "JR073") bracketed, at the 5' end, by a segment of cereal (barley) genomic DNA taken upstream from a known α-amylase structural sequence and, at the 3' end, by another genomic DNA segment containing a terminal-processing signal for the same α-amylase sequence. For each construct, the segment containing the regulatory element was about 1.5 kb in length, while the segment comprising the terminal-processing signal was about 215 bp.

As shown in FIG. 1, illustrative construct No. JR083 incorporated a segment containing a promoter ("Amy32b promoter"), which segment had been positioned just upstream of a known barley α-amylase gene described by Rogers and Milliman, *J. Biol. Chem.* 259: 12234–12240 (1984). Construct No. JR117 (not shown) included construct No. JR083 and additional exogenous DNA included for experimental purposes.

EXAMPLE 2

Obtaining Genetically-Modified Monocot Plants and Screening Seeds for Transformed Aleurone Tissue INJECTION OF EXOGENOUS DNA AND ANALYSIS OF TRANSFORMANTS: A solution of plasmid DNA (100 µg/ml in distilled water; total volume of 300 µl) produced in accordance with FIG. 1 was injected just above a developing floral node when that structure was at or just above the third leaf in a tiller with five leaves. Based on morphological criteria, the corresponding developmental time was adjudged to be about two weeks before anthesis.

Seeds produced by injected tillers were harvested and placed individually into wells in a 96-well microtiter dish. To screen for production of thaumatin, the tip of each seed opposite the embryo (about ⅕ the volume of the seed) was cut off and placed in an identical position in a duplicate dish. The remaining ⅘ of the seed was stored at 4° C. for use, as needed, for germination and growth of a plant.

The smaller fragments were sterilized by treatment with 70% ethanol (1 minute) and with 0.2% silver nitrate solution (20 minutes), respectively, and then allowed to air dry for 30 minutes. To each well was added 100 µl of incubation buffer (20 mM sodium succinate (pH 5.2), 10 mM CaCl$_2$, 10$^{-6}$M GA, 100 µM leupeptin, 50 µg/ml carbenicillin and 125 µg/ml Fungizone®, an antibiotic to inhibit fungal growth). Under these incubation conditions, the aleurone layers were activated and vigorously secreted α-amylase.

Incubation at room temperature, in a humidified atmosphere, continued for two or three days (the time of incubation differed in different experiments and was not critical for the outcome). Thereafter, 50 -µl aliquots from each well were transferred onto a replica of the microtiter plate made by sandwiching nitrocellulose membrane (Schleicher & Schuell, New Hampshire), wet with distilled water, in a 96-well "dot blot" apparatus (Bethesda Research Laboratory). After all samples were filtered through the nitrocellulose, the individual wells were washed with 150 µl of TBS.

Pursuant to the methodology of Mundy & Rogers (1986), the resulting Western dot blots were subjected to an enzyme-linked assay (ELISA) for material recognized by antithaumatin antiserum (see below). Color reactions were allowed to proceed so that negative controls still had no color background or a very faint background.

To produce rabbit antithaumatin antibodies for use in Western dot-blot screening, a mixture of thaumatins I and II, referred to hereafter as "thaumatin," was purchased from Sigma Chemical Company (Cat. No. T7638) and cross-linked with glutaraldehyde, in accordance with Bollum, Proc. Nat'l Acad. Sci. U.S.A. 72:4119–122 (1975). Thaumatin I and thaumatin II differ at five amino acid positions and have slightly different pI's.

More specifically, 3 mg of rabbit albumin were dissolved in 0.4 ml of 0.15M NaCl/0.05M Tris-HCl solution (TBS; pH 7.9). To this were added 40 µl of a 10 mg/ml solution of thaumatin in distilled water, followed with 100 µl of 21 mM glutaraldehyde (Sigma Chemical Co.) added dropwise over a total time period of one hour. The tube was allowed to incubate at room temperature overnight, and then the cross-linked proteins were dialyzed against 1 l of TBS at 4° C. for six hours.

A volume of the protein solution containing 100 µg was then emulsified with an equal volume of complete Freund's adjuvant and injected at multiple sites subcutaneously in a New Zealand White rabbit. The rabbit was boosted with antigen in incomplete Freund's adjuvant at two week intervals until an adequate antibody titer was obtained. In initial experiments, the antiserum obtained was used without further purification in screening for transformed seeds. Later, to minimize nonspecific background in Western blot analyses of proteins produced by transformed plants, antithaumatin antibodies were affinity-purified.

This purification was carried out on a thaumatin-sepharose affinity column carrying 5 mg thaumatin/ml cyanogen bromide-activated Sepharose 4B (Sigma Chemical Co.), and coupling of protein was effected according to the manufacturer's direction. Rabbit serum was heat-inactivated at 56° C. for fifteen minutes, cooled on ice, and then passed through the column at room temperature. The column was washed with TBS until the $A_{280}$ of the effluent dropped to background. Specifically, adsorbed immunoglobulins were eluted with 0.2M glycine/HCl (pH 2.2), dialyzed against TBS, and then stored in aliquots at −20° C.

Seed remnants were planted that corresponded to the foregoing test dots that appeared to be above background levels. When the plants grown from these remnants were large enough to tolerate removal of about 0.5–1 g of leaf tissue, that portion was removed and genomic DNA was isolated, pursuant to the methodology of Dellaporta et al. in MOLECULAR BIOLOGY OF PLANTS: A LABORATORY COURSE MANUAL 36–37 (Cold Spring Harbor Laboratory, 1984). The isolated DNA was then digested with restriction enzymes, electrophoresed, and transferred to Zetaprobe® nylon membrane (Biorad) for Southern-blot analysis, pursuant to Whittier et al., Nucleic Acids Res. 15: 2515–35 (1987), with a probe derived from the thaumatin-coding cDNA of Edens (1982). The stringency of the wash conditions, 0.1×SSC–0.1% SDS at 65° C., was high, and control DNA did not hybridize to the probe. The results of the screening and Southern blotting are shown in Table 1 below.

TABLE 1

| Construct | No. of seeds screened | No. of seeds planted | No. of viable seeds | No. positive Southern blot |
|---|---|---|---|---|
| 083 | 576 | 16 | 13 | 1 |
|  | 480 | 8 | 7 | 5 |
| 117 | 96 | 7 | 6 | 3 |

A pair of representative Southern blots is presented in FIG. 2; these are from gels run in parallel. In FIGS. 2A and 2B, the DNAs were digested with HindIII and EcoRI, restriction enzymes that cut the intact construct such that the promoter-gene-terminator sequences (about 2.4 kb) are freed from surrounding DNA. In FIG. 2C and 2D, the DNAs were digested with NotI and EcoRI; these should give a different pattern depending upon the relative position of sites accessible to these enzymes in the plant DNA.

Figure 2A:
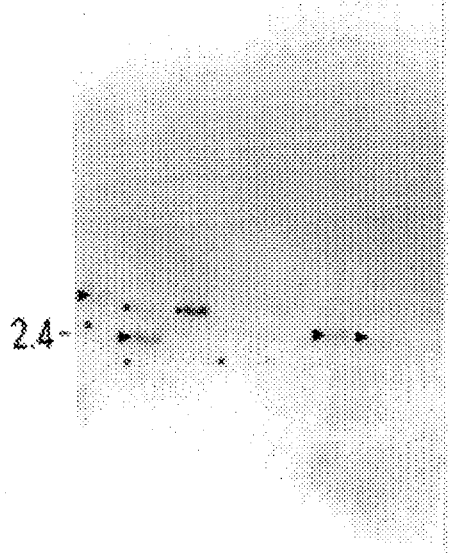
FIG. 2 is a representation of a Southern-blot hybridization analysis of DNA from control (untransformed) barley plants and plants transformed in accordance with the present invention.
Figure 2B:
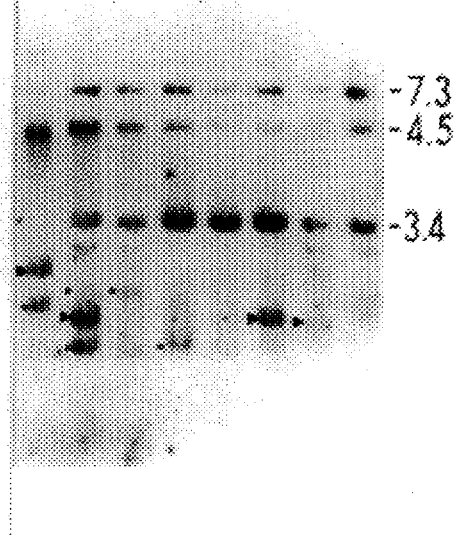
Figure 2C:
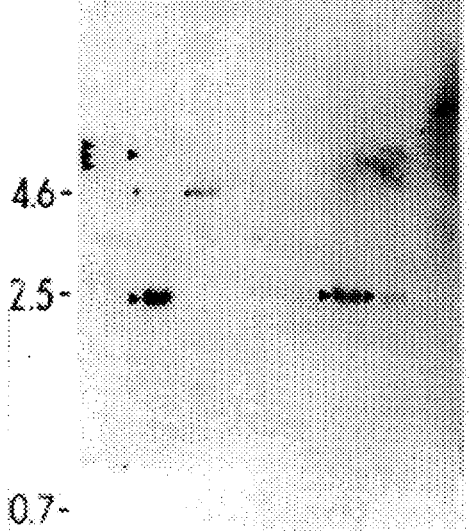
Figure 2D:
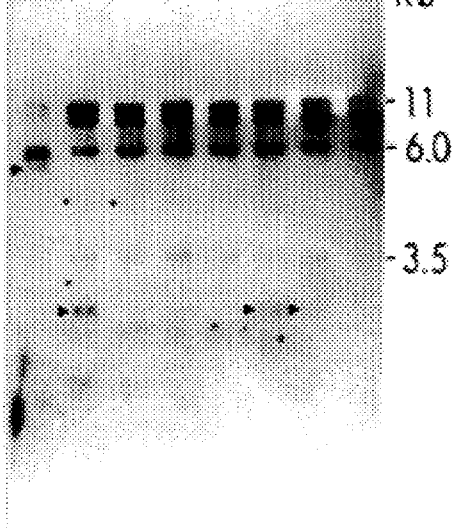

The blots were first hybridized with the thaumatin coding-sequence probe (FIG. 2A and 2C). After the membranes were washed extensively at 65° C. in 0.015M NaCl/0.00015M sodium citrate/0.1% SDS solution, they were exposed for twenty-four hours at −80° C. with an intensifying screen. The membranes were heated (100° C. in the aforementioned buffer for fifteen minutes), and thereafter exposed for three days with an intensifying screen, to ensure that all probe was removed.

The membranes were then rehybridized (FIGS. 2B and 2D) with a probe derived from a low-pI α-amylase cDNA corresponding to "clone E" described by Rogers and Milliman, J. Biol. Chem. 258: 8169–74 (1983). This cDNA is approximately 93% identical to the low-pI α-amylase genomic clone containing the amy32b promoter, and the sequence similarity is highly conserved in the 3' untranslated region. Therefore, if the genetic construct introduced into the transformed plant chromosome was intact, a restriction fragment generated from the plant DNA, using the above-mentioned enzymes, should hybridize both to the thaumatin probe and to the "clone E" cDNA probe.

The DNAs used on the blots were from: [1] plant "G12," which was a 117-series transformant and the parent plant (p) of four progeny plants that germinated from G12 seed (of ten planted); [2] two plants, designated "10D1" and "12H2," from the 083-series transformants; and [3] from a plant (C) that was grown alongside the others, but was not transformed. In every instance, DNA from the control plants did not hybridize to the thaumatin probe, although the expected hybridization of endogenous amylase genes with the "clone E" probe was observed, demonstrating that adequate amounts of DNA were indeed present on the filter.

The G12 parent and two progeny plants, Nos. 2 and 7, and plants 10D1 and 12H2 all yielded DNA with fragments that hybridized both to the thaumatin and the clone E probes. Thus, it was understood that these plants were transformants, and that the exogenous DNA was heritable to the second generation.

Seeds were tested from two 083-series transformants, 10D1 and 12H2, and from an $F_2$ generation plant ("G12-2") from the 117-series plant G12. For each plant, eighty-five aleurone layers, plus layers from a nontransformed control, were labeled for twenty-four hours with [$^{35}$S]methionine, and aleurone proteins which were antigenically related to thaumatin were selected from the culture media on individual antithaumatin-sepharose affinity columns.

Figure 3:
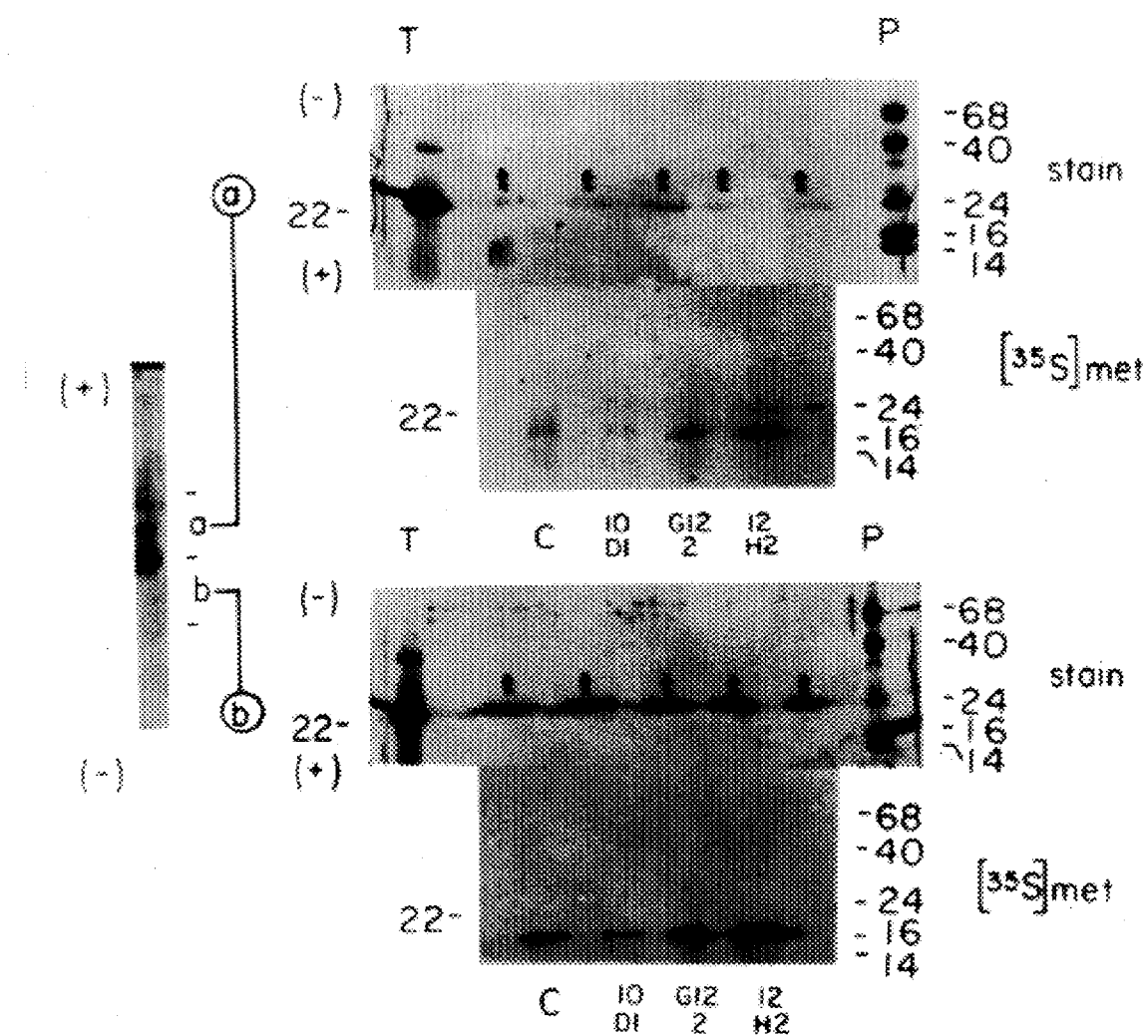
FIG. 3 is a representation of a gel-electrophoretic analysis of proteins secreted, respectively, by control barley plants and transformed plants within the present invention.

These proteins were analyzed sequentially in two different electrophoretic systems. First, the proteins were loaded onto an acid-urea gel in the order: 5 μg thaumatin marker (T), control proteins, T, 10D1, T, G12-2, T, 12H2, T, T. When the pyronin Y marker dye reached the bottom of the gel, the gel was cut vertically between the right-most two T marker lanes. The single T marker lane was electroblotted onto polyvinyldifluoride (PVDF) membrane (Immobilon®; product of Millipore Corp.) and stained with Coomassie Blue to identify the position of that protein. The appearance of that marker lane is presented in FIG. 3, left portion, where the orientation corresponding to the direction of electrophoresis is top (+) to bottom (−). The thaumatin marker (Sigma Chemical Co.) always contained three different species of proteins, with the major component electrophoresing ahead of two minor species.

The remaining portion of the gel was cut into two portions, indicated by (a) and (b), where (a) included 1 cm containing the trailing portion of the main marker band and the two minor components; (b) included 1 cm containing the main marker band and the portion of the gel immediately in front of it. Each of these strips was then individually equilibrated with the proper buffer and placed into a long horizontal well of a standard sodium dodecyl sulfate-polyacrylamide gel (SDS-PAGE), and the proteins within the strip were electrophoresed, in the (−) to (+) direction, to separate them according to molecular mass.

On either side of the strips, in separate wells, were loaded thaumatin marker (left) and a mixture of 5 other marker proteins of differing molecular masses (right). (The numbers on either side of the panels indicate the molecular mass of these markers in kilodaltons.) When the marker dye reached the bottom of the gel, electrophoresis was terminated and the gel contents were electroblotted onto a PVDF membrane. The proteins were stained with Coomassie Blue, and then the newly synthesized proteins were identified by autoradiography.

Each of FIGS. 3(a) and 3(b) is a representation of the stained membrane (top) and its autoradiograph (below). The positions of the marker proteins are indicated for the autoradiographs; these positions were confirmed by cutting out the appropriate bands from the membranes and re-exposing to x-ray film (not presented). In (a), it can be seen that the two minor thaumatin marker bands migrating more anodally in the acetic acid-urea gel are indistinguishable in size to the bulk of thaumatin (22 kd) on SDS-PAGE, since the only stained protein band in those lanes (indicated by "t" above each) migrates with that marker. This result indicates that the bands represented species of thaumatin with different overall charges but with substantially similar molecular masses, a result to be expected in light of the previously mentioned fact that "thaumatin" is a mixture of slightly different forms.

The autoradiograph demonstrates that the 12H2 sample contained a labeled protein that electrophoresed in the same manner as did the thaumatin markers (arrow). This protein (approx. 22 kd) was not present in control (C), 10D1, or G12-2 samples.

Further evidence for the specificity of this ~22 kd 12H2 protein was obtained by analyzing proteins synthesized in aleurone tissue but not secreted. Thaumatin is a storage protein and might be expected to accumulate in protein bodies in aleurone cells. Accordingly, aleurone layers from two hundred de-embryonated half-seeds from a control plant (C) and from 12H2, respectively, were incubated in the presence of [$^{35}$S]methionine and GA for forty-eight hours. After harvesting the media, indicated by "m" in FIG. 4, the aleurone layers were washed with distilled water and then homogenized with a tissue homogenizer in 20 ml of TBS solution (0.15M NaCl/0.05M Tris-HCl; pH 7.9) containing 1 mM phenylmethylsulfonyl fluoride, 100 μM leupeptin and 2% insoluble polyvinylpyrrolidone. This cell extract is indicated by "E" in FIG. 4.

The samples were diluted to 50 ml with TBS and made 0.1% with respect to NP40. Insoluble debris was removed by centrifugation in a desk centrifuge for ten minutes, and to each supernate was added 0.25 ml of 20% NP40, a detergent product sold by Shell Oil Co. The supernates were each incubated overnight, at 4° C. on a rotating shaker, with 1.5 ml of antithaumatin-sepharose, 1 ml of which contains about 9 mg of rabbit immunoglobulin selected by adsorption to a thaumatin-sepharose affinity column. After an extensive washing with TBS—0.1% NP40, proteins specifically adherent to the column were eluted with 0.2M glycine—HCl (pH 2.2) and then precipitated with 10% trichloroacetic acid. Proteins were similarly selected from the media samples.

The precipitated protein samples were dissolved in sample buffer and loaded onto an acetic acid-urea gel in two sets: in one set, 20% of each sample was loaded sequentially, followed by two consecutive wells containing 5 μg each of thaumatin marker; the second set, separated by empty wells on either side from thaumatin markers was made up of the remaining 80% of each sample. The lanes containing thaumatin marker proteins are indicated by "T" or "t" in FIG. 4. After electrophoresis, the gel was cut vertically between the two center thaumatin marker lanes. The portion of the gel containing the first set of samples was electroblotted onto PVDF membrane and stained to visualize the transferred proteins.

Figure 4A:
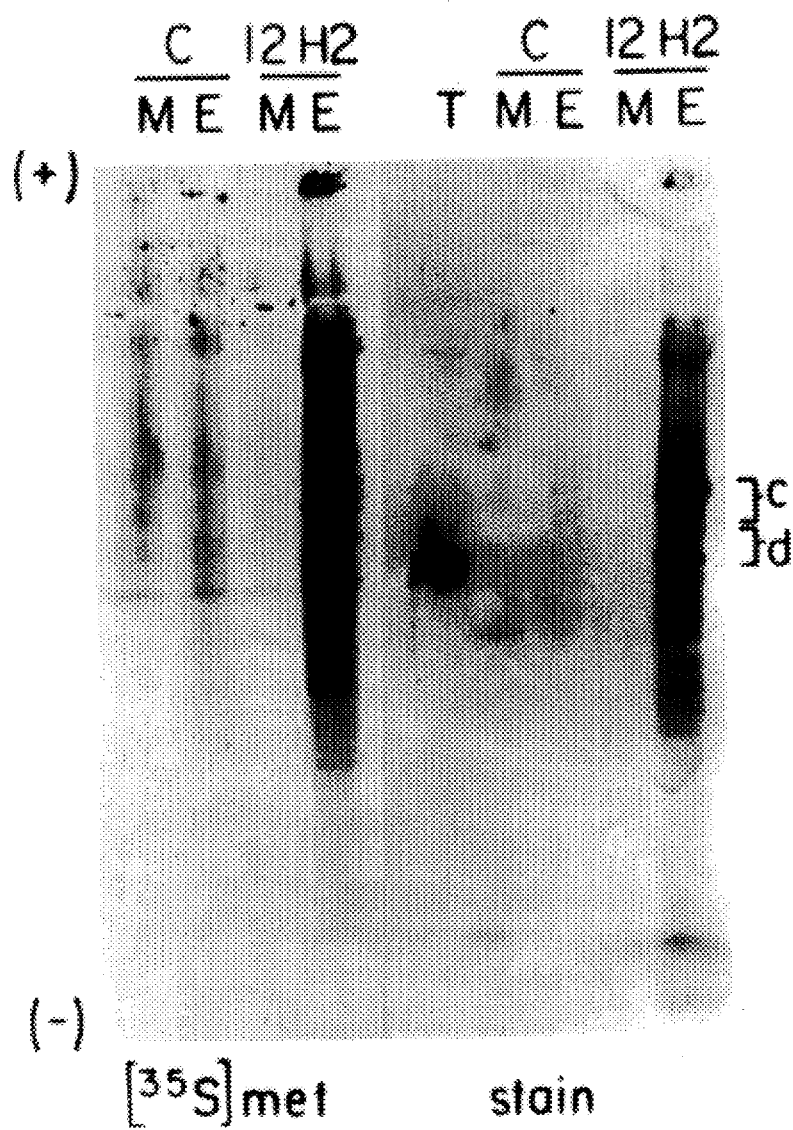
FIG. 4A is a representation of a Western blot of stained proteins produced, respectively, by a control barley plant and transformed plants within the present invention; 4B is an autoradiograph of the same Western blot.

A representation of this blot, with its autoradiograph, is presented in FIG. 4A. The remaining half of the gel was cut horizontally into two strips: strip 'd' was 0.5 cm wide and included the trailing portion of the thaumatin marker; strip 'c' included the 0.5 cm of gel immediately to the anodal side of strip 'd'. These two strips of gel included two prominent stained protein bands in the 12H2 extract sample lane that are not visualized in the other sample lanes.

The two gel strips, 'c' and 'd', were equilibrated with SDS-PAGE buffer and inserted horizontally, side-by-side, into a long well of a 2 mm-thick gel for SDS-PAGE analysis. Strip 'c' was cut to include only the four lanes containing the barley proteins. Strip 'd' included the portions of the gel with thaumatin marker protein (indicated by "t") bracketing the four lanes with barley proteins. On either side of the long well containing the gel strips were single wells loaded with thaumatin marker protein (indicated by "T", left), and a protein marker mixture (indicated by "P", right).

Figure 4B:
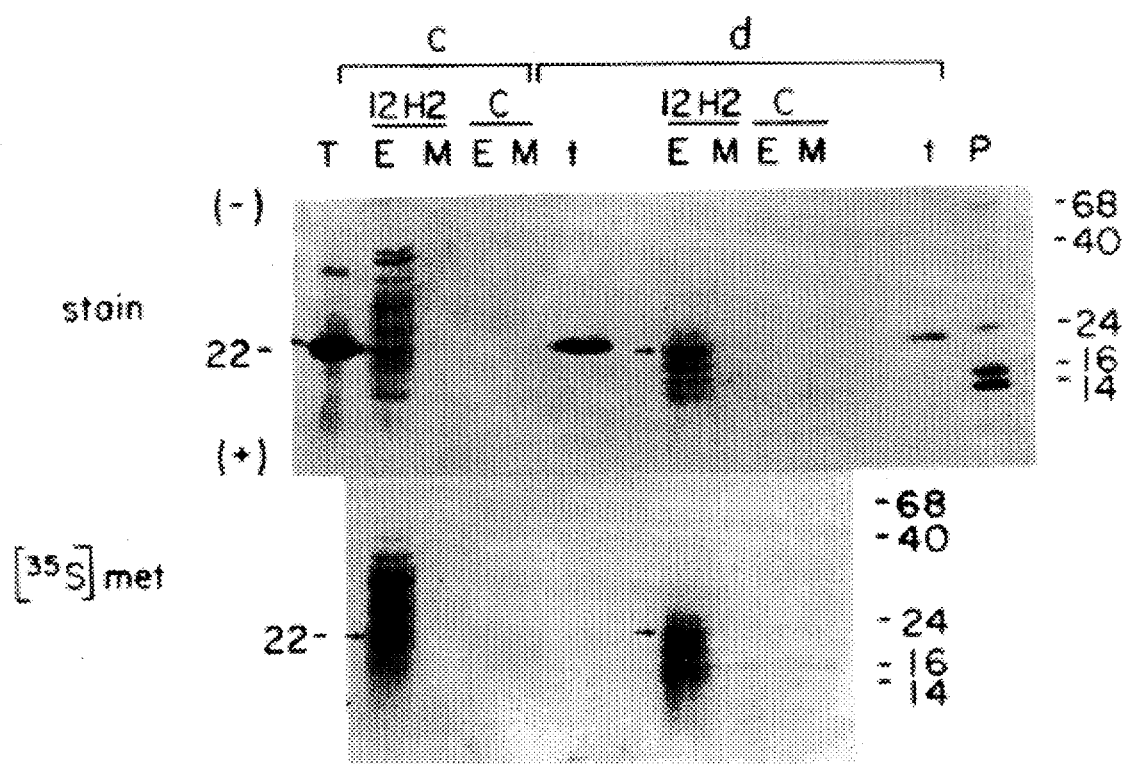

After electrophoresis, the proteins from the SDS-PAGE gel were electroblotted onto PVDF membrane and visualized by protein stain and by autoradiography (FIG. 4B). It was observed that the lane from the 12H2 extract in both strips contained proteins that resolved into multiple bands on SDS-PAGE. In strip 'd', the major protein band visualized by stain (arrow) electrophoresed identically to the internal thaumatin marker (t); on the autoradiograph, this protein band was labeled with [$^{35}$S]met. Upon prolonged exposure with fluorography, a faint band of identical size was visualized in the 12H2 medium lane, but not in the control lanes; this result was consistent with the observations described in relation to FIG. 3. All lanes from this strip had a labeled protein (>16 kd) in roughly equal amounts, demonstrating that the absence of other labeled proteins in the control lanes was not due to inadequate sample loading. The 12H2 extract lane in strip 'c' also contained a labeled protein that electrophoresed identically to the thaumatin marker (arrow).

These results demonstrate that a plant, 12H2, carrying an apparently intact recombinant gene, produced seeds that synthesized a protein in their aleurone layers that was very similar in charge to (as assessed on acetic acid-urea gel electrophoresis) and indistinguishable in size (as assessed on SDS-PAGE) from thaumatin. The observed expression in aleurone tissue was what would be predicted from the amylase promoter sequences fused to the recombinant thaumatin structural sequence. The protein encoded by the latter sequence was recognized by antithaumatin antibodies and was not present in extracts from control aleurone layers. A newly synthesized protein with these same characteristics was also secreted from 12H2 aleurone layers.

EXAMPLE 3

Use of *E. coli* β-Glucuronidase (GUS) as a Marker to Detect Transformed Plants

PRODUCTION OF RECOMBINANT DNA SEGMENTS WHEREIN THE GUS CODING SEQUENCE IS UNDER TRANSCRIPTIONAL CONTROL OF A KNOWN ALEURONE PROMOTER SEQUENCE: Construction of plasmids JR124, JR129, and JR133 is schematically presented in FIG. 5. For the JR124 construct (FIG. 5A), the coding sequence of *E. coli* β-glucuronidase (GUS) was bracketed by the Amy32b promoter/upstream sequences and the Amy32b 3' sequences for RNA processing/poly(A) addition. For the JR129 construct (FIG. 5B), the promoter/upstream sequences and part of the coding sequence for the barley gene Aleurain were fused to the GUS coding sequence. For the JR133 construct (FIG. 5C), the GUS coding sequence was fused to the N-terminal coding sequence of the barley α-amylase gene, Amy6-4. The completed construct brackets the fused coding sequence between the Amy6-4 upstream/promoter region and the Amy6-4 3' sequences for RNA processing/poly(A) addition. An example of the use of GUS in the Agrobacterium-mediated transformation of dicot plants has been described in Jefferson et al., *EMBO J.* 13:3901–3907 (1987).

TRANSFORMATION OF CEREAL WITH GUS CONSTRUCT: Barley tillers were injected with purified plasmid DNA (100 µg/ml in distilled water) as described in EXAMPLE 2.

SCREENING FOR GUS ACTIVITY: Seeds were prepared for screening essentially as described in EXAMPLE 2. Grain to be screened was cut with a razor blade to remove ca. ⅓ of the grain end opposite the plant embryo. The seed end was then placed in a well of a 96-well microtiter dish. The remaining portion of each seed containing the embryo was placed in an identical position in a duplicate dish for later use. When initiating screening, grain ends were first sterilized by washing in 70% EtOH for 1 minute, then in 0.2% $AgNO_3$ for 20 minutes, by adding the solutions to microtiter dish wells and aspirating as appropriate. The seed ends were subsequently allowed to completely dry in a sterile tissue culture hood to ensure that fungal spores are killed.

To each well containing sterile seed ends, 100 µl of incubation buffer (20 mM sodium succinate (pH 5.2), 10 mM $CaCl_2$ containing $10^{-6}$M $GA_3$, 50 µg/ml carbenicillin, and 120 µg/ml amphotericin B (Fungizone®)) was added. Incubation of the sterile seed ends and a row of ends (12) from control seeds continued for two days at room temperature in a humidified chamber.

For assaying GUS activity, 4-methyl-umbelliferyl-β-D-glucuronide (MUG) was added, to a final concentration of 1 mM, to the incubated media samples. The samples were then allowed to incubate overnight at room temperature in a humidified atmosphere to prevent evaporation. Subsequently, media samples were removed and transferred to identically-positioned wells in a fresh microtiter dish. To the media in each well, 5 µl of 2N NaOH was added and mixed gently. The resulting media were placed on a long-wavelength (>300 nm) UV light and positives exhibited a blue fluorescence. Photographs were taken using a Wratten #3 filter.

To each well was added 25 µl of homogenization buffer (50 mM $NaPO_4$ (pH 8), 10 mM EDTA, 0.1% NP40, 0.1% sarkosyl, and 1 mM phenyl methyl sulfonyl fluoride (PMSF) containing 1 mM MUG). Each seed portion was then thoroughly ground with a teflon pestle to ensure separation of the cells of the aleurone layer. Additional homogenization buffer (100–150 µl) was added to each well and the samples were incubated overnight at room temperature. Subsequently, 50 µl of media were removed from each well, transferred to an identically-positioned well in a new microtiter dish, supplemented with NaOH as above, and viewed under UV light.

To confirm possible positives, the remainder of each grain was imbibed overnight, planted, and allowed to grow until the plant was large enough to produce sufficient leaf DNA for Southern-blot analyses as described in EXAMPLE 2.

Figure 6A:
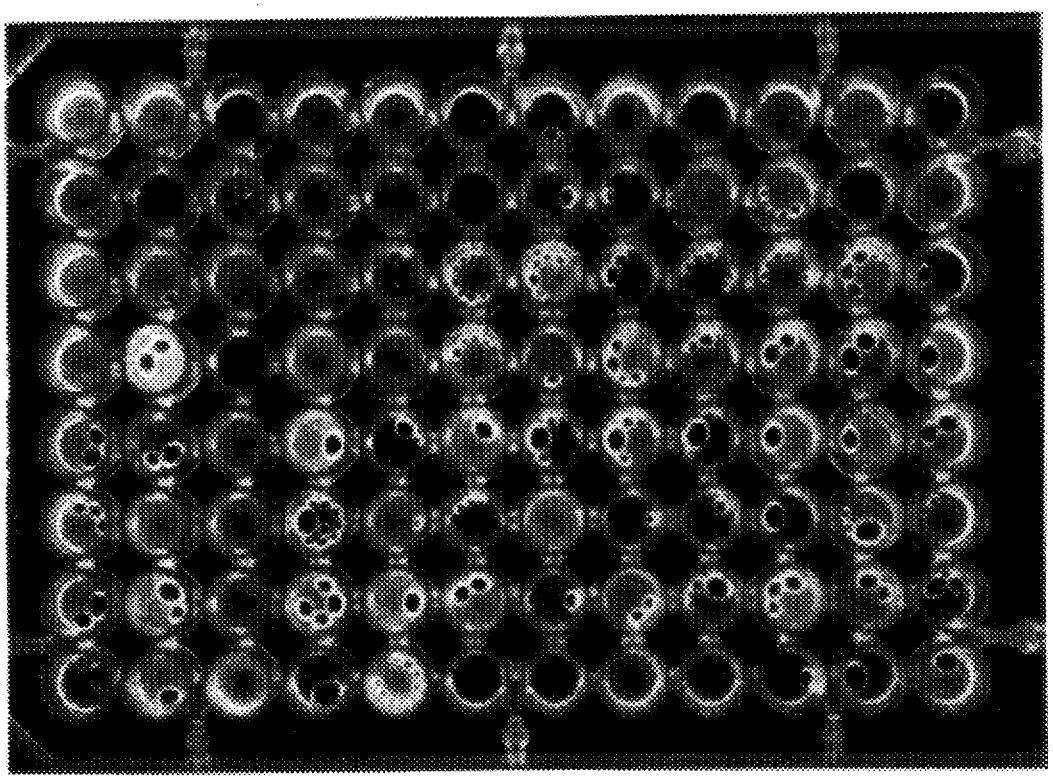
FIG. 6 is a collage of two photographs depicting, respectively, fluorescence in the media (FIG. 6A) and in extracts (FIG. 6B) in a screening plate of barley seed ends obtained from tillers injected with the JR124 construct.
Figure 6B:
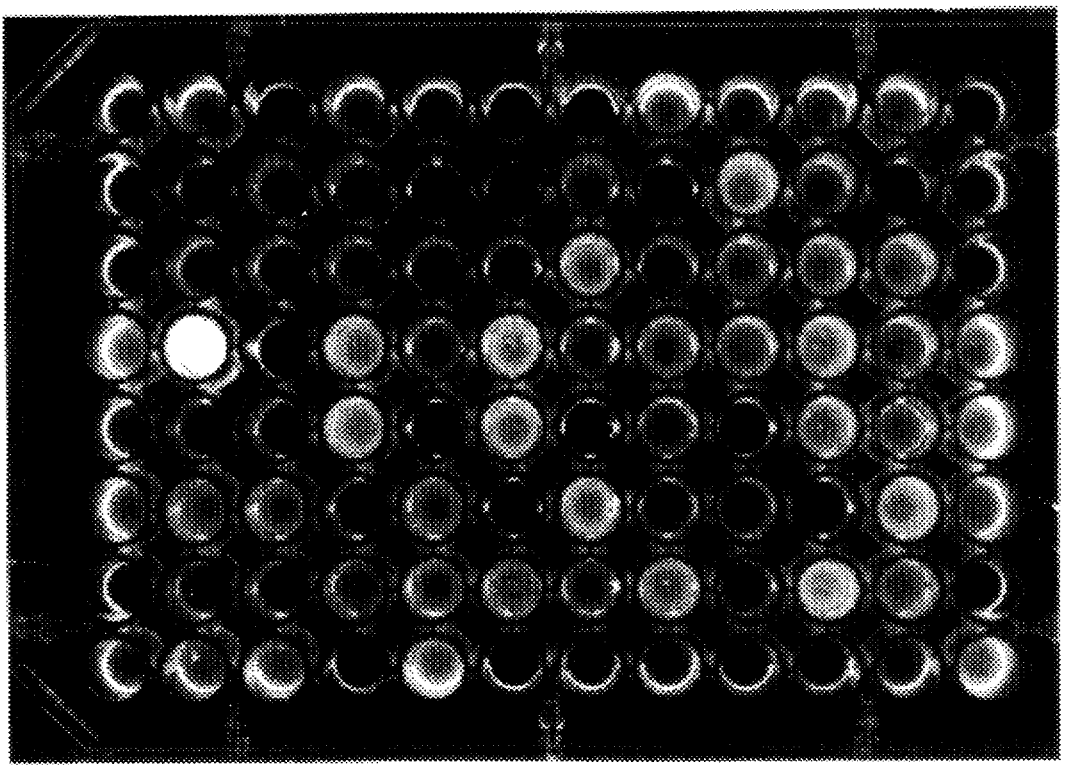

REPRESENTATIVE EXAMPLES OF POSITIVE RESULTS FROM GUS SCREENING ASSAYS: FIG. 6 depicts the media (FIG. 6A) and extracts (FIG. 6B) from screening plate #2 of seeds from tillers injected with JR124. The results demonstrate that well D2 fluoresces the brightest in both media and extracts, while well E4 may also give a positive result. The variable amounts of starchy material carried over during the transfer process from the enzyme incubation plate to the plate for alkanization and viewing can account for the light-appearing wells in the plate with extracts (FIG. 6B). These light-appearing wells are easily distinguished from the blue fluorescence in wells D2 and E4 (identified in subsequent figures as 124-2D2 and 2E4, respectively).

Seeds from tillers injected with construct JR129 were screened at the same time. Fluorescence for the positive seed 129-6B3 in media and extract samples was similarly identified, but was less intense than that of the 124 positives (124-2D2 and 2E4) .

Figure 7:
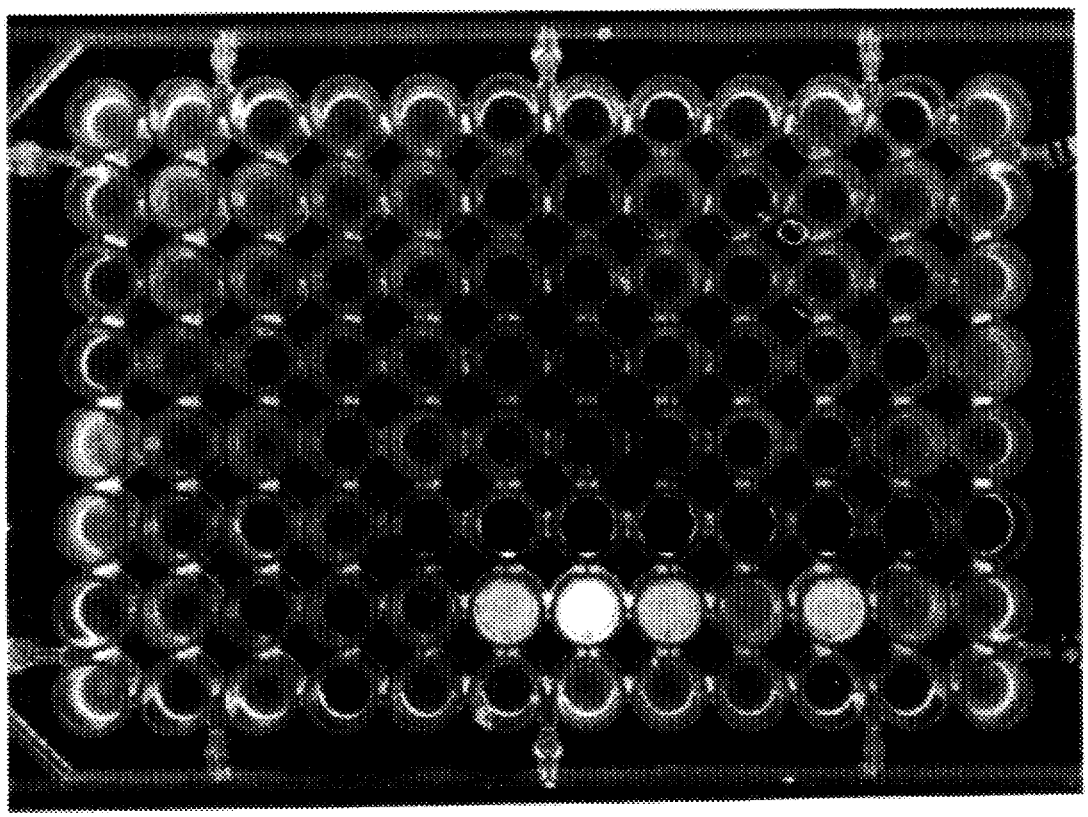
FIG. 7 is a representative assay of tissue extracts from barley seed ends from tillers injected with the JR133 construct.

FIG. 7 presents results from assaying barley seed ends from tillers injected with construct JR133 for tissue extracts only (the media from the seed end incubations was not screened). Wells G6, G7, G8, and G10 (referred to in subsequent figures as 133-2G6, 2G7, 2G8, and 2G10, respectively) exhibited strong fluorescence as seen in comparison with wells containing extracts from control seeds (E1-7) and empty wells (F5-12). The remaining wells contained assay samples from test seeds that were judged to be negative.

Figure 8:
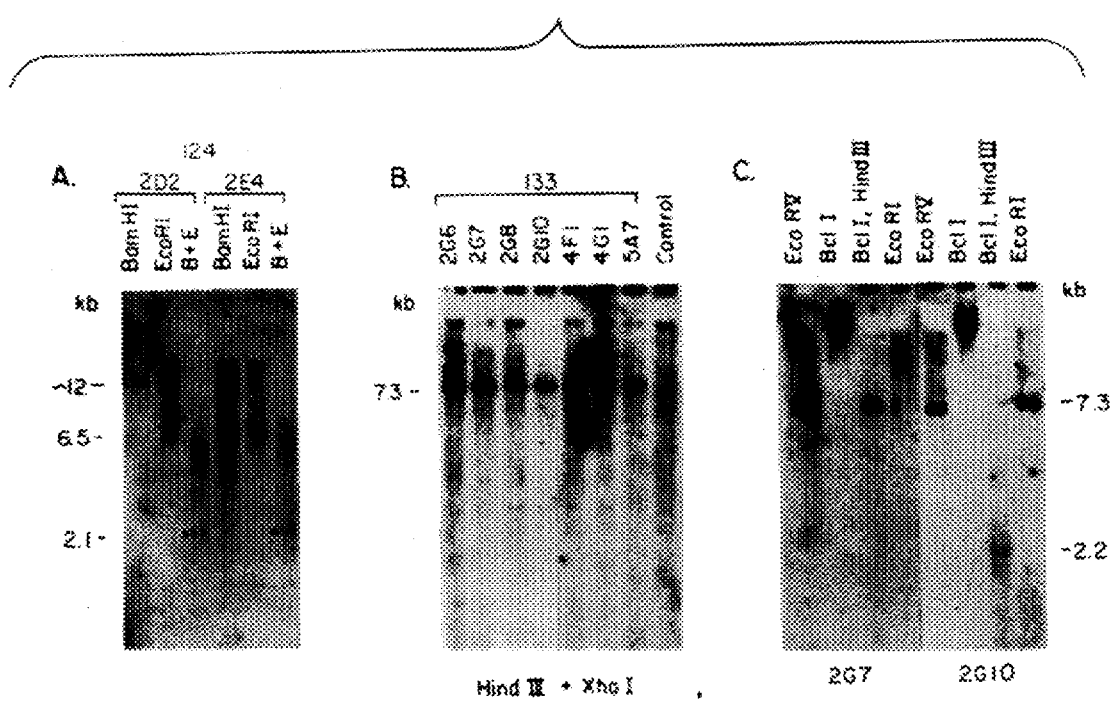
FIGS. 8A–8C provides the results from hybridizing Southern blots of DNA from two JR124 construct transformants (124-2D2 and 124-2E4) with a probe derived from the GUS coding sequence.

EVIDENCE THAT POSITIVE-SCREENING PLANTS CARRY THE INSERTED CONSTRUCT: FIG. 8A provides the results from hybridizing Southern blots of DNA from two JR124 construct transformants 124-2D2 and 124-2E4 (A), with a probe derived from the coding sequence of GUS. DNA from the two transformed plants was digested with BamHI, with EcoRI, or with a combination of both enzymes. Electrophoresis, transfer to a nylon membrane, and hybridization were performed as described above. The results indicate that the GUS probe hybridized to a ~6.5 kb EcoRI fragment in each DNA preparation. When the DNAs were digested with a combination of enzymes, the probe hybridized to a ~2.1 kb fragment (arrow) in each transformed plant; this is what was expected from the original construct if it were intact in the barley chromosomal DNA. For the DNA digestions with BamHI, two fragments in the 2D2 plant hybridize (~12 kb and ~2.5 kb), while for plant 2E4, only one (~6.5 kb) fragment was identified. This finding is consistent with different positions and/or different final arrangements of the inserted genes in the barley chromosome. DNA from control plants did not hybridize to the GUS probe in this manner.

In a similar experiment conducted with DNA derived from the plant (well 6B3) transformed with DNA from the JR129 construct, the GUS probe identified a ~6.5 kb fragment in both BamHI and EcoRI digests, and a ~2.1 kb fragment in the DNA digested with a combination of the restriction enzymes. These results are consistent with the structure of the original transforming construct.

On the basis of the GUS screening assay, seven putative positive transformed seeds (2G6, 2G7, 2G8, 2G10, 4F1, 4G1, and 5A7) were germinated and tested for the presence of the inserted gene by Southern-blot analysis. FIG. 8B shows the results from different digests of the JR133 construct hybridized with the same GUS coding sequence probe. FIG. 8B demonstrates that all the different DNAs that were digested with a combination of HindIII and XhoI gave a hybridizing fragment to the GUS probe of ~7.3 kb whereas the control DNA did not have this fragment. An identically sized fragment was generated by HindIII alone; whereas XhoI does not cut barley DNA prepared by this technique.

To ensure that other restriction enzyme sites expected for this construct were present, DNA from two additional seeds (2G7 and 2G10) was further characterized (FIG. 8C). These results demonstrate that the enzyme BclI also cut the DNA preparations poorly; the GUS probe hybridized to a high molecular weight smear of uncut DNA in each preparation treated with BclI. This indicates that the transforming DNA is integrated into the large barley chromosomal DNA and does not represent contaminating plasmid DNA which would have migrated further into the gel producing a discrete band.

Digestion of DNA from 2G7 with the restriction enzyme EcoRV produced four closely spaced fragments. This result, in combination with the results in FIG. 8C from digestion with HindIII and XhoI, suggests that the transforming DNA formed tandemly arranged repeats of itself before integrating into the barley chromosomal DNA. This result has been well-documented for DNA transfected into tobacco protoplasts. See, e.g., Czernilofsky et al., *DNA* 5: 101–113 (1986).

In contrast to the results from the digestion of DNA from 2G7, digestion of DNA from isolate 2G10 with the same restriction enzyme (EcoRV) produced only a single hybridizing band. Further, another difference is that the combination digest with HindIII and BclI for 2G7 produced a result consistent with the inability of BclI to cut most sites in barley DNA, whereas the combination digest for 2G10 produced a smaller fragment, ~2.2 kb, as well as a fragment slightly larger than 7.3 kb. These results conform to what would be expected for different transformants where the foreign DNA was integrated into different places in the chromosomal DNA.

EXAMPLE 4

Figure 9:
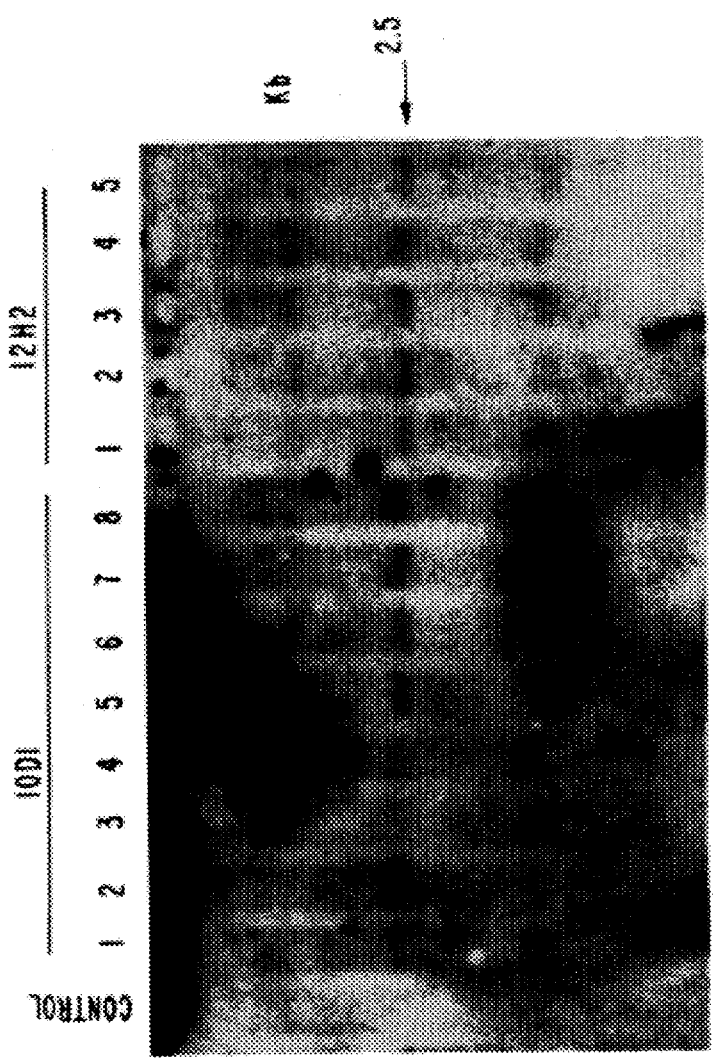
FIG. 9 presents the autoradiograph of a Southern blot of control barley DNA (C) and DNA for the $F_2$ generation progeny of the thaumatin transformants 10D1 and 12H2 hybridized with a thaumatin probe.

Stable Inheritance of Phenotype Encoded by a (G+C)-Rich, Aleurone-Transforming Construct FIG. 9 presents the autoradiograph of a Southern blot of control barley DNA (C) for the $F_2$ generation progeny of the thaumatin transformants 10D1 and 12H2. The DNA samples were digested with restriction enzymes HindIII and EcoRI together [All progeny utilized in inheritance experiments are products of self-pollination.] The blot was hybridized with a thaumatin probe. The results demonstrate that the 10D1 and 12H2 progeny have a 2.5 kb hybridizing band diagnostic of the thaumatin transformation marker which is lacking in the control, indicating that the thaumatin sequence is stably inherited. Further, tests have been done that clearly show stable inheritance for as far as the third in-bred generation (two generations each for 10D1 and 12H2, and three generations for the G12 plants described in EXAMPLE 2).

EXAMPLE 5

Lack of Stable Inheritance of Phenotype Encoded by an (A+T)-Rich, Aleurone-Transforming Construct Original DNA preparations were made from the "parent" GUS transformants, that is, from the primary transformants. Parent DNAs were prepared when the plants had two tillers and when the smaller tiller was estimated to be about 2 grams. At this stage, the second tiller (smallest) was then removed and used for DNA preparation. When the first seeds were mature, 12 seeds from each transformant 124-2D2 and 133-2G7, -2G8, -2G10, -5A7, were planted. These seeds were all derived from the first (largest) tiller that developed because they were the first to mature. Additionally, more DNA from the parents was subsequently prepared in anticipation of progeny-parent blot comparisons.

JR133 TRANSFORMANTS: DNAs from all plants that germinated were analyzed. Only one seed from 2G8 germinated, and the resultant plant was negative (data not presented).

Figure 10:
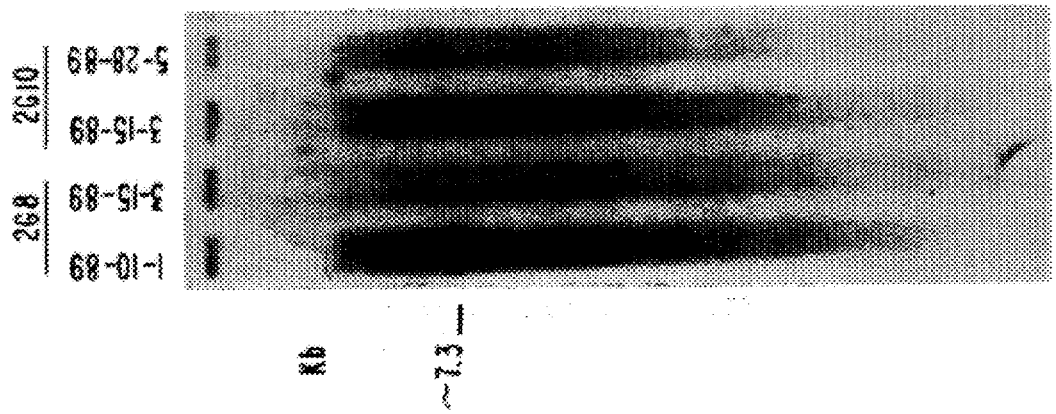
FIG. 10 presents the autoradiograph of a Southern blot, demonstrating instability of constructs containing the GUS sequence in transformed plants.

All 2G10 progeny, and the repeat preparation of parent DNA were negative. The original 2G8 preparation was compared with a subsequent preparation. In addition, the blot also contained two preparations of 2G10 parent DNA (FIG. 10). This figure shows that DNA first prepared from the 2G8 parent has a ~7.3 kb GUS-hybridizing band, while the other 3 samples were negative. Similar analyses were performed on 2G7 and 5A7 parent and progeny DNAs. None of the 2G7 or 5A7 progeny DNAs had a ~7.3 kb hybridizing band, but 2G7#3 and 5A7#8 each had a small, ~0.5–0.7 kb fragment that hybridized strongly to GUS. Control DNA from a plant grown alongside the test plants was included in all blot analyses and was always negative.

Figure 11:
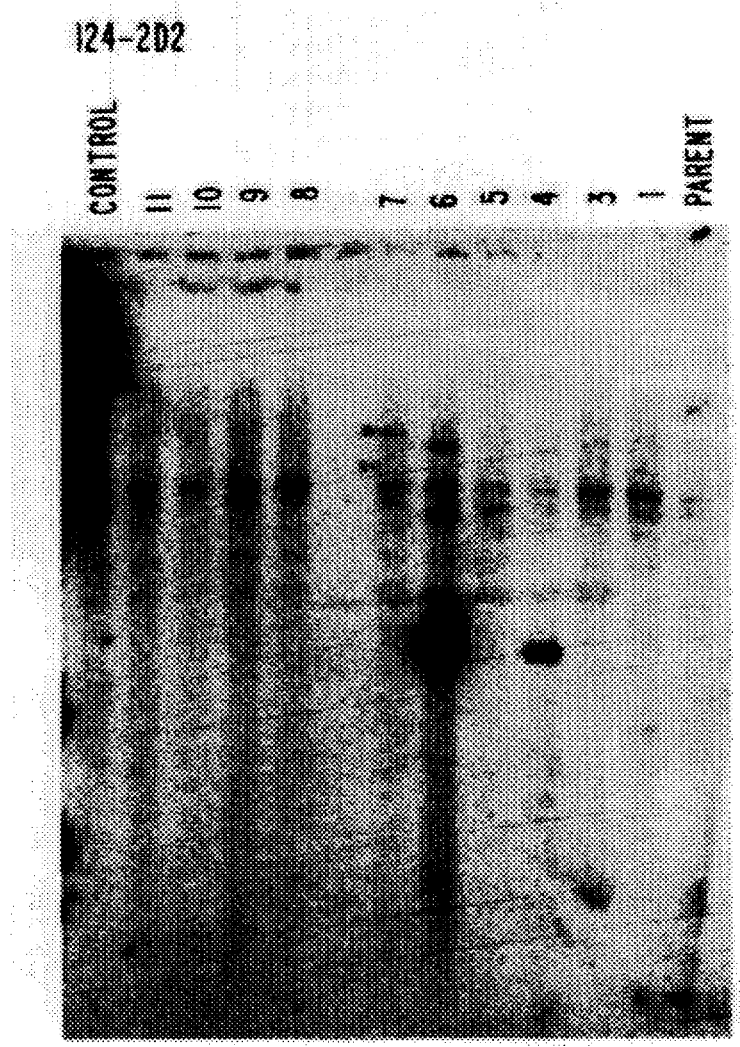
FIG. 11 presents a Southern blot autoradiograph that demonstrates that GUS sequences were lost from tissues taken from later growth of the JR124-2D2 plant, but were inherited by some of the progeny germinated from seeds of the first tiller of JR124-2D2.

JR124-2D2 PEDIGREE: Consistent with previous results, the parent DNA isolated from tissue developing later lacked hybridizing sequences (FIG. 11). Progeny numbers 4, 6, and 7 had bands on a BamHI-EcoRI digest that hybridized to GUS; for progeny numbers 4 and 6 3 and 5, the strongest bands were the expected 2.1 kb size, while progeny 6 and 7 also had large hybridizing fragments (arrows). The brackets (FIG. 11) indicate DNA fragments ~5 kb in size that are present in all of the samples, including the control, that cross-hybridized to the probe in this experiment. The intensity of the 2.1 kb bands was greater than would have been expected for single copy sequences.

These results demonstrate that the original transforming DNA identified in the parent plants was lost during plant development. This loss may have occurred in meristematic cells (regions of active mitosis and cell division) where the tissue was negative when mature. In the 133 series, small remnants of the original transforming DNA was identified in two progeny, but no intact constructs were present. For 124-2D2, the DNA was also lost from the parent, but some progeny retained large fragments that hybridized to GUS. All progeny exhibited evidence of gene rearrangement, and two progeny appeared to have multiple copies of the marker gene.

JR129 TRANSFORMANTS: GUS marker DNA was also lost from the parent, and ten progeny tested were all negative.

ANALYSIS OF HYBRIDIZING DNA IN UNSTABLY TRANSFORMED PLANTS: In order to confirm the stability results, the structure and methylation patterns of hybridizing DNA were analyzed in the 133-series parents that were GUS-positive and in the 124-2D2#6 DNA which appeared to have multiple copies. These methylation patterns were then compared to those occurring in $F_2$ and $F_3$ generation plants that were positive for the thaumatin marker. Additionally, the structures of the small hybridizing fragments identified in 2G7#3 and 5A7#8 were analyzed.

Figure 12:
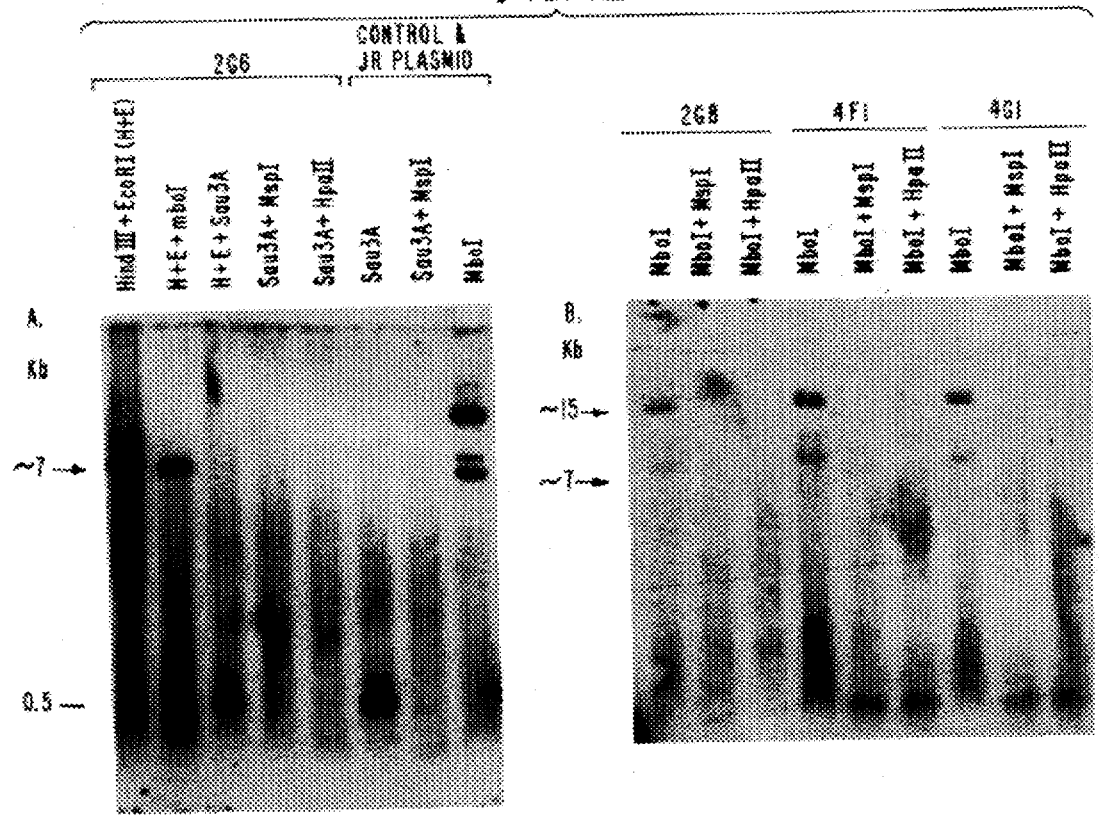
FIG. 12 presents the results of a Southern-blot analysis of hybridizing DNA in plants transformed according to the present invention.

First, the methylation pattern of the 133 -series GUS-positive parent DNA fragments in 2G6 was determined and then compared to an equal amount of control DNA spiked with ~3 copies per haploid genome of JR133 plasmid DNA (FIG. 12). Restriction enzymes that have the same recognition site (so-called isoschizomers), but that have different responses to methylation of residues in that site were used. For 2G6 (FIG. 12A), HindIII produced a ~7.3 kb band; the band remained the same size following digestion with HindIII plus MboI. In contrast, the MboI isoschizomer, Sau3AI gave the expected 500 bp hybridizing fragment. A combination digest with Sau3AI and HpaII (lane 4) or MspI (lane 5) cleaved the Sau3AI fragment to much smaller fragments. The results in FIG. 12A indicate that the hybridizing sequences in 2G6 are methylated at adenine residues that would inhibit MboI, but are not methylated at cytosine residues that would inhibit HpaII and MspI.

GUS-hybridizing DNA in undigested 2G6, 4F1, and 4G1 remained with high molecular DNA at the top of the gel (not shown). This result is consistent with data presented in FIG. 8C for 2G7 and 2G10. FIG. 12B demonstrates that MboI releases the GUS-hybridizing fragments in 2G8, 4F1, and 4G1 to give ~15 kb and ~7 kb fragments in each (lanes 1, 4, 7). The combination of MboI and MspI (lanes 2, 5, 8), or MboI and HpaII (lanes 3, 6, 9), results in loss of the large fragments with the generation of ~200 bp hybridizing fragments in each, but 4F1 has a discreet ~1 kb hybridizing fragment (lanes 5 and 6) indicating that some cytosine residues were methylated.

These data indicated that all 133 parent DNAs tested had the marker DNA present in a high molecular-weight form that could not be separated from chromosomal DNA by gel electrophoresis when uncut. Further, the N-6 methyladenine sensitive enzymes, MboI and BclI, cut only a limited number of sites (presumably because the others were methylated), and there was a defined topography of methylation surrounding the marker sequences because MboI released the markers from high molecular weight DNA, giving two discrete fragments in each instance. Additionally, the fact that the 7.3 kb Hind fragment in 2G6 was not cut by MboI indicates that the sites releasing the large fragments are in flanking DNA outside the marker sequences. Two enzymes sensitive to 5-methylcytosine were able to digest the marker DNA extensively, but the presence of small discrete fragments, such as that seen in 4F1, indicate that some cytosine residues may be methylated.

Figure 13:
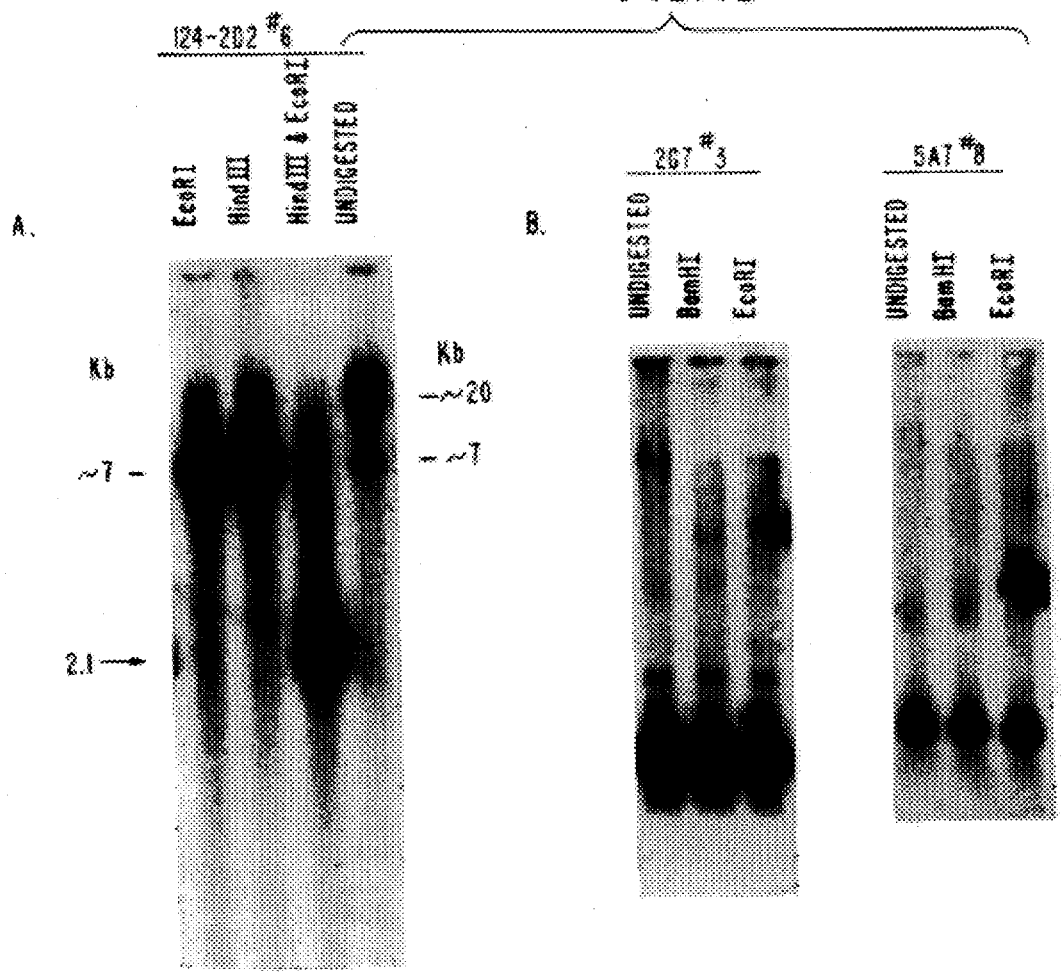
FIGS. 13A–13B provides the Southern-blot hybridization results of the undigested major GUS-hybridizing sequences separated from bulk chromosomal DNA of 124-2D2#6 compared with those fragments resulting from digestion with EcoRI or HindIII.

124-2D2#6: The major GUS-hybridizing sequences were present on two large fragments that separated from the bulk chromosomal DNA when electrophoresed without digestion (FIG. 13A). The size of the smaller, ~7 kb band was indistinguishable in size from the much stronger hybridization patterns obtained with either HindIII or EcoRI alone. These results indicate that the larger band is composed of repeats of the 7 kb hybridizing sequence that were released by HindIII and EcoRI digestion. These fragments were MboI resistant, but were apparently completely digested by either HpaII or MspI (not shown).

SMALL GUS-HYBRIDIZING FRAGMENTS IN 2G7#3 AND 5A7#8: FIG. 13B demonstrates that the GUS-hybridizing fragments are free from undigested chromosomal DNA, and that their size did not change when digested with either BamHI or EcoRI.

Figure 14:
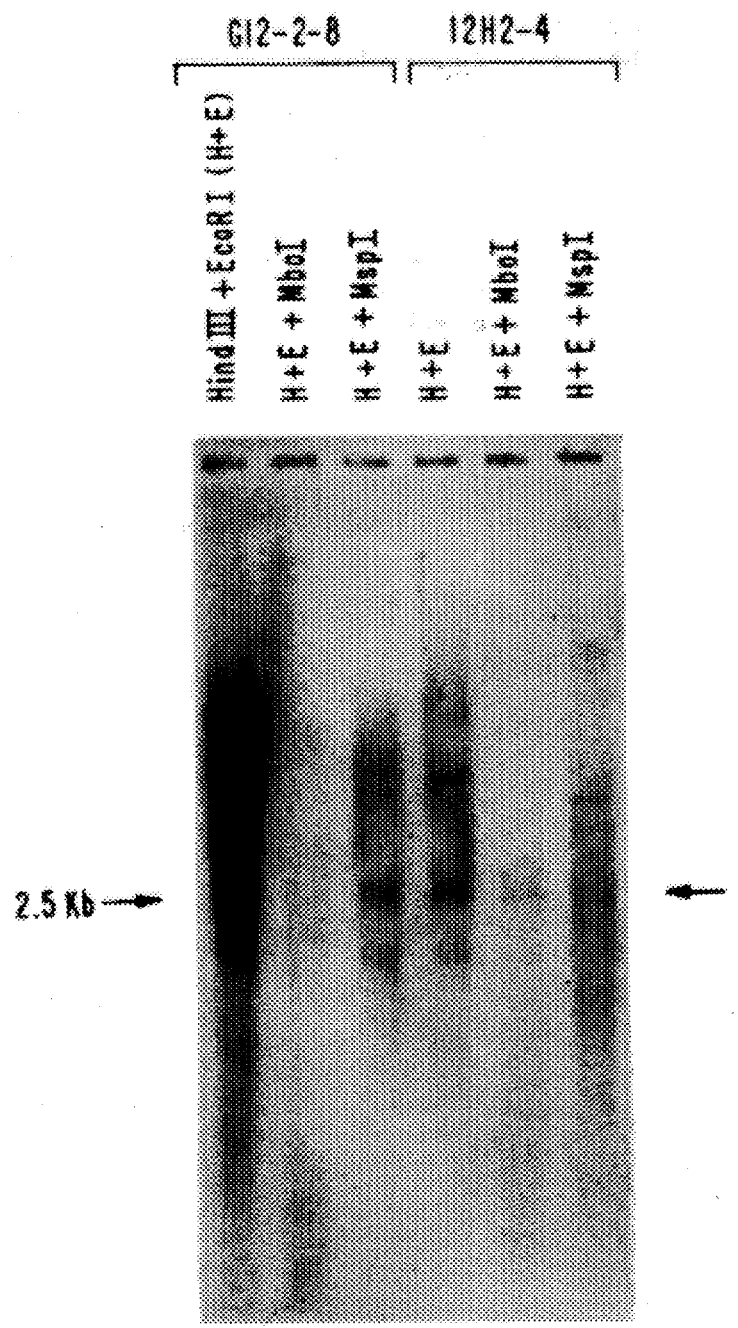
FIG. 14 provides the results of methylation in the 2.5 kb HindIII-EcoRI fragment hybridizing to the thaumatin probe in DNA from the $F_3$ plant, G12-2-8, and the $F_2$ plant, 12H2-4, using MboI and MspI.

ANALYSIS OF METHYLATION IN DNA FRAGMENTS HYBRIDIZING TO THE THAUMATIN MARKER: Analysis of methylation in the 2.5 kb HindIII-EcoRI fragment hybridizing to a thaumatin probe in DNA from the $F_3$ plant, G12-2-8, and the $F_2$ plant, 12H2-4, was performed using MboI and MspI (FIG. 14). For both samples digested with a combination of the restriction enzymes, a 2.5 kb hybridizing fragment was produced. Following digestion with HindIII and EcoRI plus MspI, the 2.5 kb fragment was not digested completely. These results were substantially different from those obtained for the GUS-positive fragments and indicated that a substantial portion of the MboI sites in the target DNA were accessible to that enzyme, while the MspI sites were at least partly blocked.

More generally, these results showed that a transforming thaumatin gene that is stably inherited has the methylation pattern expected for most barley DNA; that is, there was little adenine methylation but some cytosine methylation. In contrast, the unstable JR133-series transforming genes, although apparently integrated into chromosomal DNA, were marked by the presence of 6-methyladenine where the GATC sequence occurred and exhibited little methylation of the cytosine residues. As the unstable transforming genes were lost, intermediate forms that were free from the chromosomal DNA and displayed various deletions could be identified.

Transient expression was thus usefully effected by means of integrated DNA characterized by extensive adenine methylation, but heritably stable integration was accomplished when such methylation was minimized. This principle can be applied in selecting or designing other genes for stable expression according to the present invention.

EXAMPLE 6

Transformation of Another Cereal (Oats)

Figure 15A:
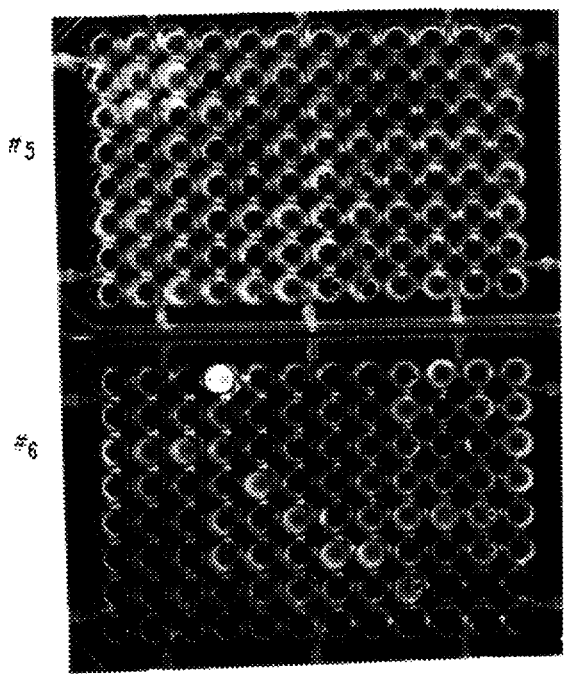
FIG. 15 presents photographs depicting fluorescence in the media (FIG. 15A) and extracts (FIG. 15B) from a screening plate of oat seed ends obtained from tillers injected with the JR133 construct.
Figure 15B:
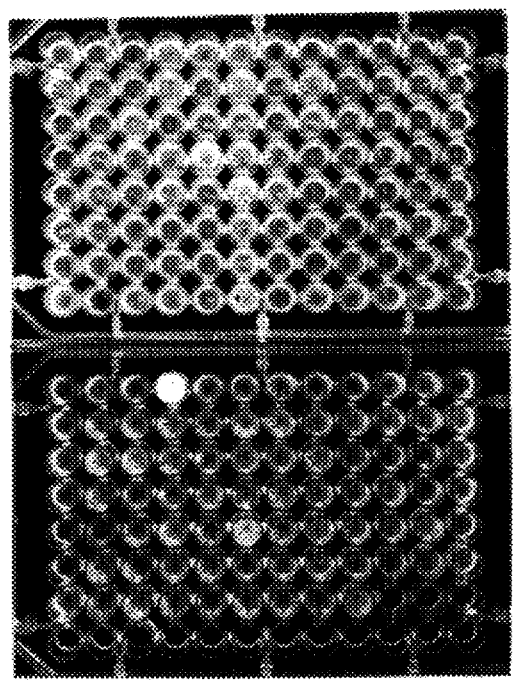

Tillers from oat plants derived from seeds (obtained from Mangelsdorf Seed Company, St. Louis) were injected with DNA as described for barley plants in Example 2. At the stage where five leaves had developed and when the developing inflorescence could be palpated at about the level of the third leaf, oat tillers were injected with DNA from construct JR133. The seeds were then screened as described for barley in EXAMPLE 2. FIG. 15 provides the results of the screen for seeds in plates 4 (only extract screen is shown), 5 (only media screen is shown) and 6. FIGS. 15A and 15B demonstrate the results for the media screen and the extract screen, respectively. The results indicate that in both the media and extract, the seed in well 6A4 exhibited a strong positive fluorescent signal indicating the presence of the transforming DNA, while the other wells did not appear to produce a positive signal.

What is claimed is:

1. A differentiated, transgenic, cereal plant that produces seeds comprised of endosperm tissue, wherein said endosperm tissue comprises a genetic construct which is comprised of a DNA sequence encoding a polypeptide that is foreign to said cereal plant and an endosperm-specific promoter, wherein expression of said DNA sequence is substantially greater in said endosperm tissue than in leaf and root tissues of said plant and wherein said cereal plant is one that produces a floral tiller.

2. A plant according to claim 1, wherein said DNA sequence is a eukaryotic or prokaryotic structural sequence.

3. A plant according to claim 1, wherein said DNA sequence encodes at least a portion of the thaumatin amino-acid sequence.

4. A plant according to claim 3, wherein said DNA sequence encodes a fusion product comprised of said portion of the thaumatin amino-acid sequence.

5. A plant that produces seeds comprised of endosperm tissue that comprises a genetic construct which is comprised of a DNA sequence encoding a polypeptide that is foreign to said cereal plant and an endosperm-specific promoter, wherein expression of said DNA sequence is substantially greater in said endosperm tissue than in leaf and root tissues of said plant and wherein said cereal plant is one that produces a floral tiller grown from a seed from a plant, wherein said plant is produced from a seed from a plant according to claim 1.

6. A plant according to claim 1, wherein said endosperm tissue is comprised of aleurone tissue which comprises said genetic construct.

7. A uniform population of cereal plants according to claim 1.

8. A uniform population of plants according to claim 6.

9. A seed of a transgenic cereal plant, wherein endosperm tissue of said seed comprises a genetic construct comprised of a DNA sequence encoding a polypeptide that is foreign to said cereal plant and an endosperm-specific promoter, wherein said cereal plant is one that produces a floral tiller and wherein expression of said DNA sequence is substantially greater in said endosperm tissue than in leaf and root tissues of said plant.

10. A plant according to claim 1, wherein expression of said DNA sequence occurs exclusively in said endosperm tissue.

11. A plant according to claim 1, wherein expression of said DNA sequence in said endosperm tissue, at some stage of development or activation, is at least about 50 times greater than in leaf and root tissues of said plant.

12. A uniform population according to claim 7, wherein expression of said DNA sequence occurs exclusively in said endosperm tissue.

13. A uniform population according to claim 1, wherein expression of said DNA sequence in said endosperm tissue, at some stage of development or activation, is at least about 50 times greater than in leaf and root tissues of said plant.

14. A plant according to claim 1, wherein said cereal plant is of a crop selected from the group consisting of wheat, barley, oats, sorghum, rye, millet, rice and maize.

15. A plant according to claim 1, wherein said genetic construct comprises a regulatory element comprised of a promoter selected from the group consisting of the Amy32b promoter, the Amy6-4 promoter, and the Aleurain promoter.

16. A differentiated, transgenic, cereal plant that produces seeds comprised of endosperm tissue, wherein said endosperm tissue comprises a genetic construct which is comprised of a DNA sequence encoding a polypeptide that is foreign to said cereal plant and an endosperm-specific promoter, wherein said cereal plant is one that produces a floral tiller and wherein expression of said DNA sequence is endosperm-specific.

17. A seed of a transgenic cereal plant, wherein endosperm tissue of said seed comprises a genetic construct comprised of a DNA sequence encoding a polypeptide that is foreign to said cereal plant and an endosperm-specific promoter, wherein said cereal plant is one that produces a floral tiller and wherein expression of said DNA sequence is endosperm-specific.

18. A plant according to claim 1, wherein said cereal plant is wheat.

19. A plant according to claim 1, wherein said cereal plant is barley.

20. A plant according to claim 1, wherein said cereal plant is oats.

21. A plant according to claim 1, wherein said cereal plant is sorghum.

22. A plant according to claim 1, wherein said cereal plant is rye.

23. A plant according to claim 1, wherein said cereal plant is millet.

24. A plant according to claim 1, wherein said cereal plant is rice.

25. A plant according to claim 1, wherein said cereal plant is maize.

26. A method for obtaining seed comprised of genetically transformed endosperm tissue, comprising the steps of:

(A) providing a genetic construct;

(B) injecting said genetic construct into a floral tiller of a cereal plant prior to anthesis in said plant, and thereafter;

(C) assaying seeds from said injected plant for the presence of an expression product of said DNA sequence in the endosperm of any of said seeds, thereby to identify a seed comprised of genetically transformed endosperm tissue, wherein said genetic construct is comprised of a DNA sequence encoding a polypeptide that is foreign to said cereal plant and an endosperm-specific promoter such that expression of said DNA sequence is greater in said endosperm tissue than in leaf and root tissues of said plant.

27. A method according to claim 26, wherein step (C) comprises assaying for said expression product by using an antibody that recognizes said expression product.

28. A method according to claim 26, wherein said promoter is selected from the group consisting of Amy32b promoter, Amy6-4 promoter and Aleurain promoter.

29. A method according to claim 26, wherein said cereal plant is selected from the group consisting of wheat, barley, oats, sorghum, rye, millet, rice and maize.

30. A method according to claim 26, wherein said DNA sequence encodes at least a portion of the thaumatin amino-acid sequence.

31. A method according to claim 30, wherein said DNA sequence encodes a fusion product comprised of said portion of said thaumatin amino acid sequence.

32. A method according to claim 26, wherein step (C) comprises assaying said seeds for the presence of an expression product of said DNA sequence in an aleurone layer of any of said seeds.

33. A process of producing a polypeptide, comprising the steps of:

(A) producing a plant as claimed in claim 1, and (B) isolating said polypeptide from said plant.

34. A process according to claim 33, wherein said genetic construct is contained in aleurone tissue.

35. A process according to claim 33, wherein step (A) comprises producing a uniform population of said cereal plants and step (B) comprises isolating said polypeptide from said uniform population.

* * * * *